US011306305B2

(12) United States Patent
Gagnon et al.

(10) Patent No.: US 11,306,305 B2
(45) Date of Patent: Apr. 19, 2022

(54) TUNING CRISPR/CAS9 ACTIVITY WITH CHEMICALLY MODIFIED NUCLEOTIDE SUBSTITUTIONS

(71) Applicants: Board of Trustees of Southern Illinois University, Springfield, IL (US); The Royal Institution for the Advancement of Learning/McGill University, Montreal (CA)

(72) Inventors: Keith Gagnon, Carbondale, IL (US); Masad Damha, Montreal (CA); Elise Malek-Adamian, Ottawa (CA); Maryam Habibian, Montreal (CA); Daniel Timothy O'Reilly, Waterlooville (GB); Zachery Kartje, Valparaiso, IN (US)

(73) Assignees: Board of Trustees of Southern Illinois University, Carbondale, IL (US); The Royal Institution for the Advancement of Learning/McGill University

( * ) Notice: Subject to any disclaimer, the term of this patent is extended or adjusted under 35 U.S.C. 154(b) by 534 days.

(21) Appl. No.: 16/327,605

(22) PCT Filed: Sep. 22, 2017

(86) PCT No.: PCT/US2017/053041
§ 371 (c)(1),
(2) Date: Feb. 22, 2019

(87) PCT Pub. No.: WO2018/057946
PCT Pub. Date: Mar. 29, 2018

(65) Prior Publication Data
US 2019/0185844 A1  Jun. 20, 2019

Related U.S. Application Data

(60) Provisional application No. 62/398,775, filed on Sep. 23, 2016.

(51) Int. Cl.
| | | |
|---|---|---|
| *C12N 15/10* | (2006.01) | |
| *A61K 48/00* | (2006.01) | |
| *C12N 9/22* | (2006.01) | |
| *C12N 15/11* | (2006.01) | |
| *C12N 15/113* | (2010.01) | |
| *C12N 15/90* | (2006.01) | |

(52) U.S. Cl.
CPC ............ *C12N 15/102* (2013.01); *A61K 48/00* (2013.01); *C12N 9/22* (2013.01); *C12N 15/11* (2013.01); *C12N 15/113* (2013.01); *C12N 15/90* (2013.01); *C12N 15/907* (2013.01); *C12N 2310/20* (2017.05); *C12N 2310/315* (2013.01); *C12N 2310/318* (2013.01); *C12N 2310/319* (2013.01); *C12N 2310/3231* (2013.01); *C12N 2310/344* (2013.01); *C12N 2310/346* (2013.01); *C12N 2800/80* (2013.01)

(58) Field of Classification Search
None
See application file for complete search history.

(56) References Cited

U.S. PATENT DOCUMENTS

| | | |
|---|---|---|
| 8,906,616 B2 | 12/2014 | Zhang et al. |
| 9,580,701 B2 | 2/2017 | May et al. |
| 9,580,727 B1 | 2/2017 | Donohoue et al. |
| 2009/0176725 A1 | 7/2009 | Morrissey et al. |
| 2016/0177304 A1 | 6/2016 | Collingwood et al. |

FOREIGN PATENT DOCUMENTS

| | | |
|---|---|---|
| WO | 2007/022369 A2 | 2/2007 |
| WO | 2015/006747 A2 | 1/2015 |
| WO | 2016/089433 A1 | 6/2016 |

OTHER PUBLICATIONS

Cummins, L.L. et al, "Characterization of Fully 2'-Modified Oligoribonucleotide Hetero-and Homoduplex Hybridization and Nuclease Sensitivity," Nucleic Acids Research, vol. 23, No. 11, Jun. 1995, pp. 2019-2024.
Manoharan, M. et al, "Unique Gene-Silencing and Structural Properties of 2'-F Modified siRNAs," Angew Chem Int Ed Engl., vol. 50, No. 10, Mar. 1, 2011, pp. 2284-2288.
Gagnon, J.A. et al, "Efficient Mutagenesis by Cas9 Protein-Mediated Oligonucleotide Insertion and Large-Scale Assessment of Single-Guide RNAs," PLOS One, vol. 9, No. 5, May 29, 2014, pp. 1-8.
International Search Report re Application No. PCT/US2017/053041, dated Jan. 22, 2018.
Written Opinion re Application No. PCT/US2017/053041, dated Jan. 22, 2018.
Ageely, E.A. et al, "Quadruplex-Flanking Stem Structures Modulate the Stability and Metal Ion Preferences of RNA Mimics of GFP," ACS Chem. Biol, 2016, 11(9): pp. 2398-2406.
Anders, C. et al, "In vitro Enzymology of Cas9," Methods Enzymol, 2014, 546: pp. 1-20.

(Continued)

*Primary Examiner* — Suzanne M Noakes
*Assistant Examiner* — Jae W Lee
(74) *Attorney, Agent, or Firm* — Husch Blackwell LLP

(57) ABSTRACT

The present disclosure provides CRISPR/Cas9 ribonucleoprotein compositions comprising chemically modified CRISPR RNA (crRNA) guide and trans-acting CRISPR RNA (tracrRNA) components. Methods of using the disclosed CRISPR/Cas9 ribonucleoprotein compositions are also provided.

14 Claims, 17 Drawing Sheets
Specification includes a Sequence Listing.

(56) References Cited

OTHER PUBLICATIONS

Bachelin, M. et al, "Structure of a Stereoregular Phosphorothioate DNA/RNA Duplex," Nat Struct Biol, 1998, 5(4): pp. 271-276.

Damha, M.J. et al, "Hybrids of RNA and Arabinonucleic Acids (ANA and 2'F-ANA) Are Substrates of Ribonuclease H," J Am Chem Soc, 1998, 120(49): pp. 12976-12977.

Du, D. et al, "CRISPR Technology for Genome Activation and Repression in Mammalian Cells," Cold Spring Harb Protoc, 2016, doi: 10.1101/pdb.prot 090175, pp. 40-49.

Fedoroff, O.Y. et al, "Structure of a DNA: RNA Hybrid Duplex. Why RNase H Does Not Cleave Pure RNA," J Mol Biol, 1993, 233(3): pp. 509-523.

Gagnon, K.T. et al, "Stepping Toward Therapeutic CRISPR," Proc Natl Acad Sci USA, 2015, 112(51): pp. 15536-15537.

Gonzalez, C. et al, "Structure and Dynamics of a DNA-RNA Hybrid Duplex with a Chiral Phosphorothioate Moiety: NMR and Molecular Dynamics with Conventional and Time-Averaged Restraints," Biochemistry, 1995, 34(15): pp. 4969-4982.

Hendel, A. et al. "Chemically Modified Guide RNAs Enhance CRISPR-Cas Genome Editing in Human Primary Cells," Nature Biotechnology, 2015, 33(9): pp. 985-989.

Jiang, F. et al, "A Cas9-guide RNA Complex Preorganized for Target DNA Recognition," Science, 2015, 348(6242): pp. 1477-1481.

Jiang, F. et al, "Structures of a CRISPR-Cas9 R-loop Complex Primed for DNA Cleavage," Science, 2016, 351(6275): pp. 867-871.

Koshkin, A.A. et al, "LNA (Locked Nucleic Acid): An RNA Mimic Forming Exceedingly Stable LNA:LNA Duplexes," J Am Chem Soc, 1998, 120(50): pp. 13252-13253.

Liang, X. et al, "Rapid and Highly Efficient Mammalian Cell Engineering via Cas9 Protein Transfection," Journal of Biotechnol, 2015, 208: pp. 44-53.

Mangos, M.M. et al, "Flexible and Frozen Sugar-Modified Nucleic Acids—Modulation of Biological Activity Through Furanose Ring Dynamics in the Antisense Strand," Top Med Chem, 2002, 2(10): pp. 1147-1171.

Mangos, M.M. et al, "Efficient RNase H-directed Cleavage of RNA Promoted by Antisense DNA or 2'F-ANA Constructs Containing Acyclic Nucleotide Inserts," J Am Chem Soc, 2003, 125(3) pp. 654-661.

Martin-Pintado, N. et al, "The Solution Structure of Double Helical Arabino Nucleic Acids (ANA and 2'F-ANA): Effect of Arabinoses in Duplex-Hairpin Interconversion," Nucl Acids Res, 2012, 40(18): pp. 9329-9339.

Martinez-Montero, S. et al, "Locked 2'-Deoxy-2',4'-Difluororibo Modified Nucleic Acids: Thermal Stability, Structural Studies, and siRNA Activity," ACS Chem Biol, 2015, 10(9): pp. 2016-2023.

Nishimasu, H. et al, "Crystal Structure of Cas9 in Complex with Guide RNA and Target DNA," Cell, 2014, 156(5): pp. 935-949.

O'Geen, H. et al, "A Genome-Wide Analysis of Cas9 Binding Specificity Using ChIP-seq and Targeted Sequence Capture," Nucl Acids Res, 2015, 43(6): pp. 3389-3404.

Rahdar, M. et al, "Synthetic CRISPR RNA-Cas9-Guided Genome Editing in Human Cells," PNAS, published online Nov. 16, 2015, 112: pp. E7110-E7117.

Salazar, M. et al, "The DNA Strand in DNA-RNA Hybrid Duplexes is Neither B-form nor A-form in Solution," Biochemistry, 1993, 32(16): pp. 4207-4215.

Sander, J.D. et al, "CRISPR-Cas Systems for Genome Editing, Regulation and Targeting," Nat. Biotechnol, 2014, 32(4): pp. 347-355.

Sternberg, S.H. et al, "Conformational Control of DNA Target Cleavage by CRISPR-Cas9," Nature, 2015, 527(7576): pp. 110-113.

Trempe, J.F. et al, "NMR Solution Structure of an Oligonucleotide Hairpin with a 2'F-ANA/RNA Stem: Implications for RNase H Specificity Toward DNA/RNA Hybrid Duplexes," J Am Chem Soc, 2001, 123(21): pp. 4896-4903.

Wahl, M.C. et al, "B-Form to A-Form Conversion by a 3'-terminal Ribose: Crystal Structure of the Chimera d(CCACTAGTG)r(G)," Nucls Acids Res, 2000, 28(21): pp. 4356-4363.

Wasner, M. et al, "Physicochemical and Biochemical Properties of 2',5'-linked RNA and 2',5'-RNA:3',5'-RNA "Hybrid" Duplexes," Biochemistry, 1998, 37: pp. 7478-7486.

Yu, X. et al, "Improved Delivery of Cas-9 Protein/gRNA Complexes Using Lipofectamine CRISPRMAX," Biotechnol Lett, 2016, 38(6): pp. 919-929.

Zuris, J.A. et al, "Efficient Delivery of Genome-Editing Proteins In vitro and In vivo," Nat. Biotechnol, 2015, 33(1): pp. 73-80.

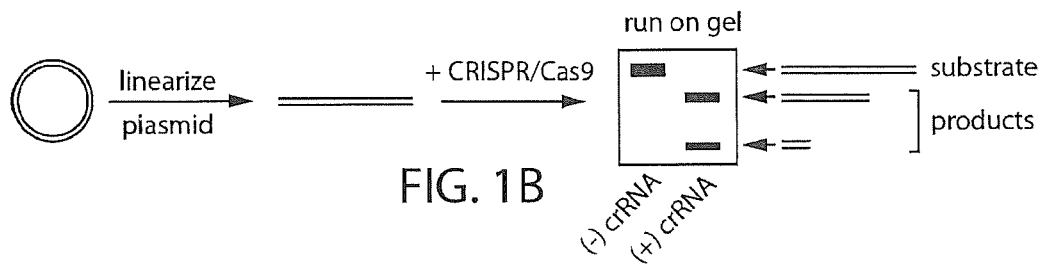
FIG. 1B
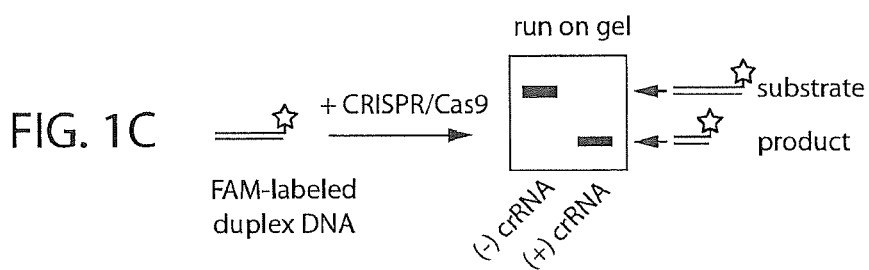
FIG. 1C
FIG. 1D
Natural dual-RNA
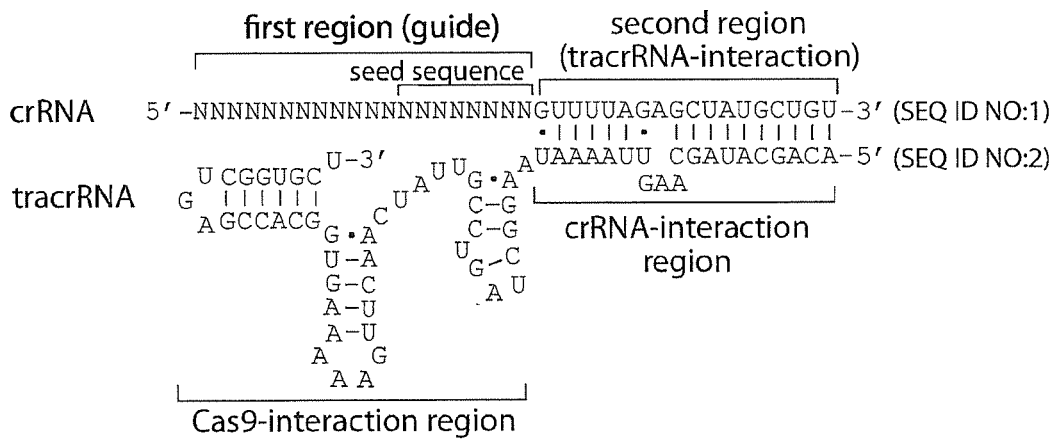
Artificial sgRNA
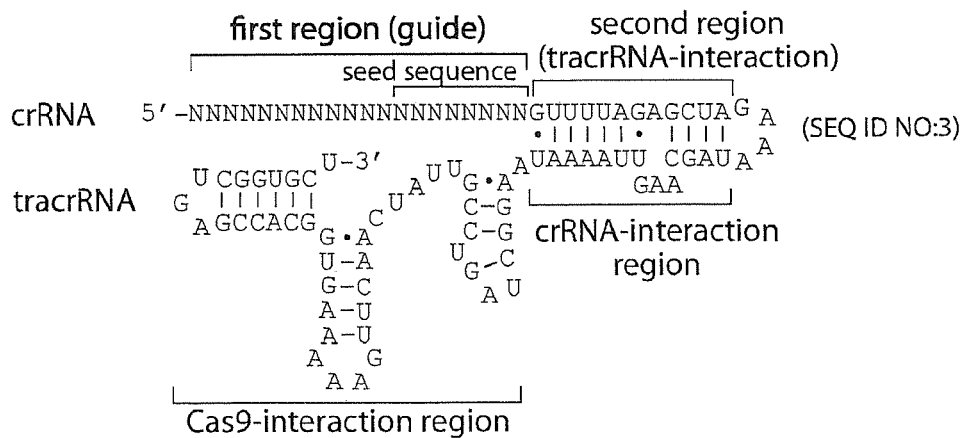

FIG. 10A
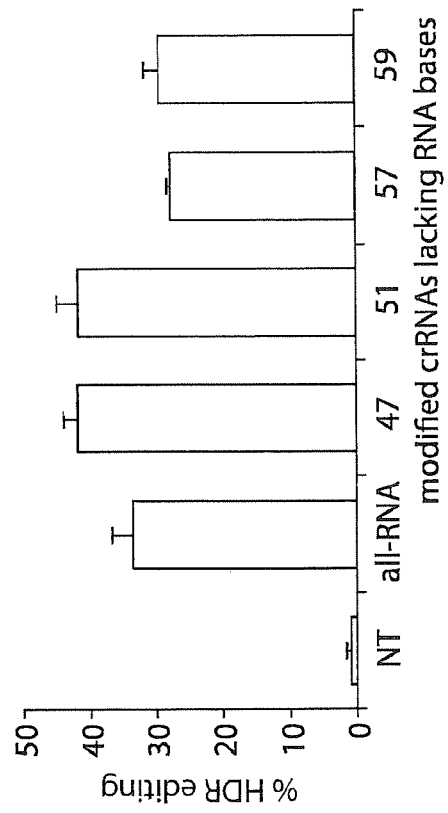
FIG. 10B
FIG. 10C
```
              10        20        30        40        50        60        70        80
              ....|....|....|....|....|....|....|....|....|....|....|....|....|....|....|....|
TR gene       ACCAAGGTGCAGAGCCAGCCCTTCTT----------------ATTCGGCCTTGAATTGATCATATGCGGATTAGAAAAACAACTT   (SEQ ID NO:14)
TR_HDR_expected ACCAAGGTGCAGAGCCAGCCTTCTTTgctgccctggatgttgttaaATTCGGCCTTGAATTGATCATATGCGGATTAGAAAAACAACTT (SEQ ID NO:15)
TR_HDR_F seq  NNNNNNNNNNNNNNGCCTTCTTTGCTGCCCTGGATGTTGTTAAATTCGGCCTTGAATTGATCATATGCGGATTAGAAAAACAACTT   (SEQ ID NO:16)
```

TUNING CRISPR/CAS9 ACTIVITY WITH CHEMICALLY MODIFIED NUCLEOTIDE SUBSTITUTIONS

CROSS-REFERENCE TO RELATED APPLICATIONS

This application is a 35 U.S.C. 371 U.S. National Stage of International Application Serial No. PCT/US2017/053041, filed on Sep. 22, 2017, which claims benefit to U.S. Provisional Application Ser. No. 62/398,775, filed on Sep. 23, 2016, all of which are incorporated herein by reference.

FIELD OF THE INVENTION

The present invention relates to CRISPR/Cas9 ribonucleoproteins comprising chemically modified CRISPR RNA (crRNA) guide and trans-acting CRISPR RNA (tracrRNA) components.

BACKGROUND OF THE INVENTION

Although CRISPR technology is revolutionizing genome editing and synthetic biology applications, predictable targeting in the laboratory and safety in the future clinic will require better mechanistic understanding and careful engineering. The prototypical CRISPR-associated protein, Cas9 from *S. pyogenes*, naturally binds two RNAs, a CRISPR RNA (crRNA) guide and a trans-acting CRISPR RNA (tracrRNA), to assemble a CRISPR ribonucleoprotein (crRNP). Improving the crRNP cleavage kinetics and stability would represent a significant advance in the art.

SUMMARY OF THE INVENTION

The present disclosure provides compositions comprising a Cas9 protein, a first oligonucleotide, referred to herein as the "crRNA portion," comprising a first region, referred to herein as the "guide region," having a 5' end, which is generally about 12 nucleotides in length, although in certain embodiments the 5' end of the first region is about 6, about 7, about 8, about 9, about 10, about 11, about 13, about 14, about 15, about 16, about 17, about 18, about 19, or about 20 nucleotides in length, and a 3' end, referred to herein as the "seed region," which is generally about 8 nucleotides in length, although in particular embodiments the 3' end of the first region is about 4, about 5, about 6, about 7, about 9, about 10, about 11, about 12, about 13, about 14 or about 15 nucleotides in length, and a second region, referred to herein as the "tracrRNA interaction region", and a second oligonucleotide, referred to herein as the "tracrRNA portion," comprising a first region, referred to herein as the "crRNA interaction region," and a second region, wherein the second region of the first oligonucleotide interacts with the first region of the second oligonucleotide, and the second region of the second oligonucleotide interacts with the Cas9 protein, wherein the first oligonucleotide comprises at least a first 2'-deoxyribonucleotide or 2'-deoxyribonucleotide analog in the second region or within about 12 nucleotides of the 5' end of the first region, the first oligonucleotide is comprised entirely of 2'-fluorinated ribonucleotides, the first oligonucleotide is comprised of a mixture of 3'5'-linked ribonucleotides and 2'5'-linked ribonucleotides, referred to herein as a "mixmer," or the first oligonucleotide is comprised of a mixture of 2'-fluorinated and 2'5'-linked ribonucleotides.

In certain embodiments, the second region of the first oligonucleotide comprises only 2'-deoxyribonucleotides or 2'-deoxyribonucleotide analogs. As used herein, the term "2'-deoxyribonucleotide analog" means a chemically modified nucleotide that maintains the properties of a 2'-deoxyribonucleotide, or mimics a 2'-deoxyribonucleotide, which in certain embodiments means that the 2'-deoxyribonucleotide analog generally favors the formation of a B-form helical structure. A number of 2'-deoxyribonucleotide analogs are well-known to the person of skill in the art and can be used in certain embodiments of the present disclosure. For example, 2'-deoxyribonucleotide analogs that can be used in certain embodiments of the present disclosure include, but are not limited to, 2'-fluoroarabinonucleotides, acyclic or unlocked nucleosides and acyclic aliphatic linkers. In particular embodiments the second region of the first oligonucleotide comprises the chemical structure of crRNA-E2_J.

In some embodiments, the first oligonucleotide comprises at least a first 2'-fluoroarabinonucleotide in the second region or within about 12 nucleotides of the 5' end of the first region. In other embodiments the first oligonucleotide comprises a plurality of 2'-fluoroarabinonucleotides in the second region or within about 12 nucleotides of the 5' end of the first region. In further embodiments the first oligonucleotide comprises a combination of 2'-fluoroarabinonucleotides, 2'-deoxyribonucleotides and 2'-deoxyribonucleotide analogs in the second region or within about 12 nucleotides of the 5' end of the first region.

In additional embodiments, the first region of the first oligonucleotide comprises at least a first ribonucleotide or ribonucleotide analog within about 8 nucleotides of the 3' end of the first region. As used herein, the term "ribonucleotide analog" means a chemically modified nucleotide that maintains the properties of a ribonucleotide, or mimics a ribonucleotide, which in certain embodiments means that the ribonucleotide analog generally favors the formation of an A form helical structure. A number of ribonucleotide analogs are well-known to the person of skill in the art and can be used in certain embodiments of the present disclosure. For example, ribonucleotide analogs that can be used in certain embodiments of the present disclosure include, but are not limited to, 2'-fluorinated nucleotides (2'-F), 2'-5'-linked nucleotides, locked nucleotides or nucleic acids (LNA), 2'-fluorinated,4'-O-methyl (2'F,4'OMe) nucleotides, 2',4' di fluorinated nucleotides, and 2',4'-di-O-methyl (2',4' diOMe) nucleotides. In selected embodiments the first region of the first oligonucleotide comprises only ribonucleotides or ribonucleotide analogs within about 8 nucleotides of the 3' end of the first region.

In certain embodiments, the second oligonucleotide comprises at least a first 2'-deoxyribonucleotide or 2'-deoxyribonucleotide analog. In additional embodiments, the first region and the second region of the second oligonucleotide comprises at least a first 2'-deoxyribonucleotide or 2'-deoxyribonucleotide analog. In further embodiments, the first region and the second region of the second oligonucleotide comprises a plurality of 2'-deoxyribonucleotides or 2'-deoxyribonucleotide analogs. In particular embodiments, the second oligonucleotide comprises the chemical structure of tracrR/DNA-C.

While most of the oligonucleotides disclosed herein have conventional phosphodiester internucleotide linkages, other internucleotide linkages are well-known to the skilled artisan and can be used in additional embodiments of the present disclosure. Thus the present disclosure also provides oligonucleotides that have one or more internucleotide linkage that is not a phosphodiester internucleotide linkage. In some embodiments, the first and/or second oligonucleotide comprises at least a first phosphorothioate, phosphotriester, phosphorodithioate, boranophosphate, Rp- and/or Sp-phosphorothioate, 3' thioformacetal, methylene, amide, methylphosphonate, phosphoramidate internucleotide linkage, or any combination thereof.

In particular embodiments, the first oligonucleotide and the second oligonucleotide are covalently linked. Such compositions are generally referred to as single guide (sg) oligonucleotides.

While the most common source of Cas9 protein is from *Streptococcus pyogenes*, other sources of Cas9 protein are well-known to those of skill in the art and can be used in some embodiments of the present disclosure. Examples of other sources of Cas9 protein include, but are not limited to, *Staphylococcus aureus*, and numerous other bacterial species.

The present disclosure also provides methods of cleaving a double-stranded DNA, comprising contacting the double stranded DNA with a composition as described herein. In certain embodiments, the double-stranded DNA is present inside of a cell. In additional embodiments, the cell is comprised within a mammal. In further embodiments, the mammal is a human subject. In embodiments where the compositions of the present disclosure are administered to a mammal or human subject, the compositions can be administered systemically, intraperitoneally, intravenously, intramuscularly, subcutaneously, intrathecally, intraventricularly, orally, enterally, parenterally, intranasally, dermally, or by inhalation. For example, administration of the presently disclosed compositions includes local or systemic administration, including injection, oral administration, particle gun or catheterized administration, and topical administration.

In certain embodiments, the compositions disclosed herein are comprised within a pharmaceutical composition with a pharmaceutically acceptable excipient or carrier. Suitable excipients, carriers and their formulations are described in Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000.

The present disclosure further provides methods of mutating a double-stranded DNA segment, comprising contacting the double-stranded DNA segment with a composition as described herein. Such mutations can be insertions or deletions of nucleotides. In some embodiments, double-stranded DNA segment is located in a cell. In additional embodiments, the double-stranded DNA segment is a genomic DNA segment.

The present disclosure additionally provides compositions comprising a Cas9 protein, a first oligonucleotide comprising a first region having a 5' end and a 3' end and a second region, and a second oligonucleotide comprising a first region and a second region, wherein the second region of the first oligonucleotide interacts with the first region of the second oligonucleotide, and the second region of the second oligonucleotide interacts with the Cas9 protein, wherein all nucleotides of the first oligonucleotide are 2'-deoxyribonucleotides or 2'-deoxyribonucleotide analogs. Such compositions are generally referred to as catalytically inactive, or dead Cas9 (dCas9). In one example of such a composition, the first oligonucleotide comprises the chemical structure of crRNA_K. In further embodiments, the first oligonucleotide comprises at least a first 2'-fluoroarabinonucleotide. In certain embodiments, the Cas9 protein comprises at least a first mutation that inactivates the Cas9 protein. In particular embodiments, the Cas9 protein comprises a D10A and/or a H840A mutation.

The present disclosure further provides methods of binding a double-stranded DNA without cleaving the double-stranded DNA, comprising contacting the double-stranded DNA with a composition comprising a Cas9 protein, a first oligonucleotide comprising a first region having a 5' end and a 3' end and a second region, and a second oligonucleotide comprising a first region and a second region, wherein the second region of the first oligonucleotide interacts with the first region of the second oligonucleotide, and the second region of the second oligonucleotide interacts with the Cas9 protein, wherein all nucleotides of the first oligonucleotide are 2'-deoxyribonucleotides or 2'-deoxyribonucleotide analogs. In some embodiments, the first oligonucleotide comprises at least a first 2'-fluoroarabinonucleotide.

The present disclosure also provides methods of inhibiting transcription of a double stranded DNA, comprising contacting the double-stranded DNA with a composition comprising a Cas9 protein, a first oligonucleotide comprising a first region having a 5' end and a 3' end and a second region, and a second oligonucleotide comprising a first region and a second region, wherein the second region of the first oligonucleotide interacts with the first region of the second oligonucleotide, and the second region of the second oligonucleotide interacts with the Cas9 protein, wherein all nucleotides of the first oligonucleotide are 2'-deoxyribonucleotides or 2'-deoxyribonucleotide analogs. In particular embodiments, the first oligonucleotide comprises at least a first 2'-fluoroarabinonucleotide. In other embodiments, the double-stranded DNA is located in a cell.

The present disclosure further provides methods of activating transcription of a double-stranded DNA, comprising contacting the double-stranded DNA with a composition comprising a Cas9 protein, a first oligonucleotide comprising a first region having a 5' end and a 3' end and a second region, and a second oligonucleotide comprising a first region and a second region, wherein the second region of the first oligonucleotide interacts with the first region of the second oligonucleotide, and the second region of the second oligonucleotide interacts with the Cas9 protein, wherein all nucleotides of the first oligonucleotide are 2'-deoxyribonucleotides or 2'-deoxyribonucleotide analogs. In certain embodiments, the first oligonucleotide comprises at least a first 2'-fluoroarabinonucleotide. In additional embodiments, the double-stranded DNA is located in a cell.

The present disclosure additionally provides compositions comprising a Cas9 protein, a first oligonucleotide comprising a first region having a 5' end and a 3' end and a second region, and a second oligonucleotide comprising a first region and a second region, wherein the second region of the first oligonucleotide interacts with the first region of the second oligonucleotide, and the second region of the second oligonucleotide interacts with the Cas9 protein, wherein all nucleotides of the first oligonucleotide are 2'-deoxyribonucleotides or 2'-deoxyribonucleotide analogs. Such compositions are generally referred to as catalytically inactive, or dead Cas9 (dCas9). In one example of such a composition, the first oligonucleotide comprises the chemical structure of crRNA_K. In further embodiments, the first oligonucleotide comprises at least a first 2'-fluoroarabinonucleotide. In certain embodiments, the Cas9 protein comprises at least a first mutation that inactivates the Cas9 protein. In particular embodiments, the Cas9 protein comprises a D10A and/or a H840A mutation.

As used herein, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B, FIG. 1C and FIG. 1D show CRISPR/Cas9 elements and cleavage. FIG. 1A shows CRISPR/Cas9 RNP assembly. FIG. 1B shows a prototypical CRISPR/Cas9 plasmid cleavage assay. FIG. 1C shows a prototypical CRISPR/Cas9 FAM-labeled duplex DNA cleavage assay. FIG. 1D shows RNA-RNA interactions of the crRNA and tracrRNA components in a natural dual-RNA CRISPR/Cas9 complex, and the regions corresponding to the crRNA and tracrRNA components in an artificial single guide RNA (sgRNA) CRISPR/Cas9 complex.

FIG. 3A shows the cleavage activity kinetics for crRNA-E2, crRNA-E2_J and sgRNA-E2. FIG. 3B is a comparison of crRNA-E2_J cleavage of plasmid with sgRNA-E2 and crRNA-E2 targeting the same sequence.

FIG. 4A shows a schematic of crRNA-E2_J and shortened versions of crRNA-E2_J, and corresponding cleavage activity toward a plasmid target shown to the right. FIG. 4B shows a schematic of crRNA:tracrRNA RNA-DNA swap mutants. FIG. 4C shows cleavage activity of RNA-DNA swap mutant combinations against plasmid and FAM duplex DNA targets.

FIG. 5A shows that different DNA targets and crRNA guides give similar cleavage patterns independent of sequence. FIG. 5B shows that DNA-substituted crRNAs are compatible with cleavage activity when using SaCas9.

FIG. 6A shows that crRNA-E2_J cleaves the same phosphodiester bonds as crRNA-E2 and sgRNA-E2. FIG. 6B shows that when compared to crRNA-E2, the crRNA-E2_J configuration exhibits a greater than 2-fold improvement in discrimination for a single nucleotide mismatch near the center of the seed sequence, a discrimination similar to that of sgRNA-E2.

FIG. 7A shows a schematic of crRNA-E2 configurations tested and the binding affinity of a pre-assembled tracrRNA-Cas9 complex for each crRNA. FIG. 7B shows binding curves demonstrating relative binding affinities of each crRNA for a tracrRNA-Cas9 complex. FIG. 7C shows binding curves of CRISPR/"dead" Cas9 (dCas9) RNP complexes binding to a duplex DNA target.

FIG. 9A shows the structure of a ribonucleotide (RNA), deoxyribonucleotide (DNA), and certain chemically modified nucleotides used in crRNAs. FIG. 9B shows configurations for chemically modified crRNAs targeting the tetracycline receptor (TR) gene. Cleavage activity of respective chemically modified crRNA-TR configurations is shown to the right, and compared to an unmodified crRNA-TR of the same sequence (dotted line).

FIG. 10A, FIG. 10B and FIG. 10C show homology-directed repair (HDR) by DNA-substituted and chemically modified crRNAs. Editing was performed by RNP transfection into HeLa cells, followed by PCR-based detection of genomic insertion of a barcoded sequence. FIG. 10A shows transfection of DNA-substituted crRNAs targeting the TR gene resulted in HDR editing. PCR products were resolved on a gel and insertion detected as a higher molecular weight band. FIG. 10B shows quantification of HDR editing by chemically modified crRNAs (numbered as shown in FIG. 9B). FIG. 10C shows results of sequencing to validate correct insertion of donor DNA into the TR gene during HDR editing.

DETAILED DESCRIPTION

Figure 1A:
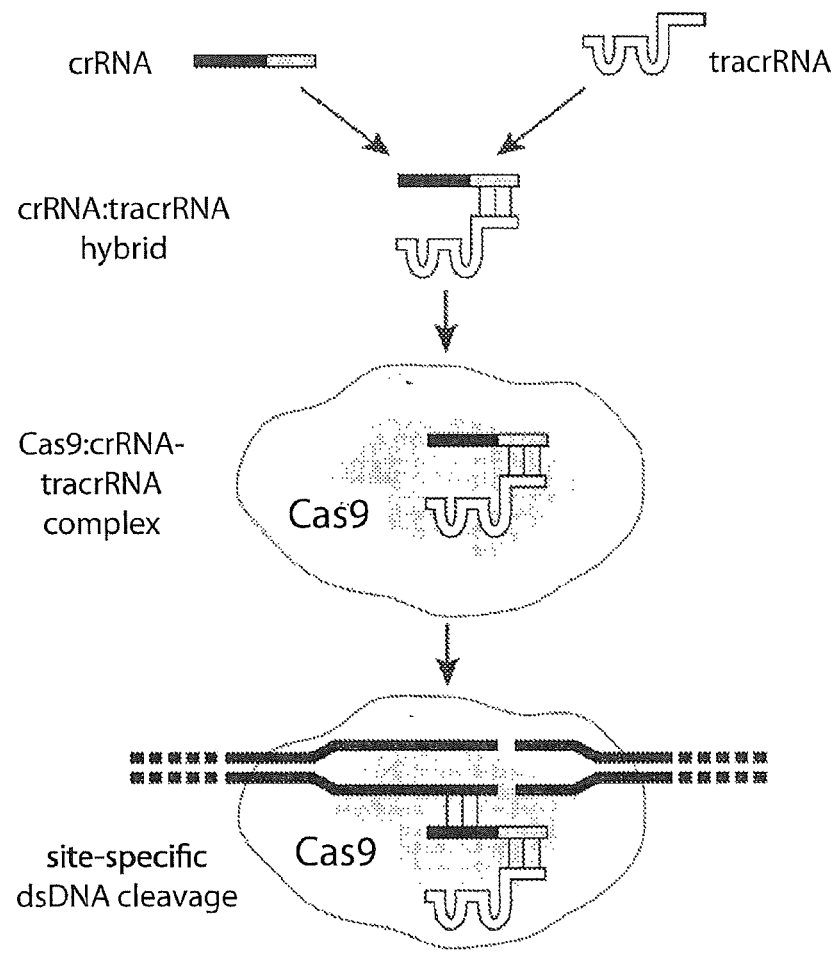

The RNA components of the CRISPR system present an opportunity to probe and tune activity through nucleotide substitutions and chemical modification. The inventors unexpectedly found that DNA substitutions in the crRNA component can significantly increase Cas9 cleavage kinetics. By judicious placement of chemical modifications and DNA bases, all RNA bases were able to be eliminated from the crRNA while maintaining cleavage. Tuning of crRNP activity appears to rely on a balance between A-form-like helical structure in the guide-target duplex and a catalytically-competent conformation of Cas9. In addition, it was found that DNA substitutions can be made in the tracrRNA component while still retaining activity. The results shown herein establish a mechanistic and biochemical rationale for how to use nucleic acid chemistry to tune Cas9 for a variety of in vitro and in vivo applications, including, but not limited to, therapeutics.

CRISPR/Cas9 is a ribonucleoprotein (RNP) component of bacterial and archaeal innate immune systems that has been recently co-opted for gene editing and genome engineering in many organisms, including humans. Therapeutic and biotechnology applications for CRISPR/Cas9 may require substantial chemical modification of the ribonucleic acid (RNA) part of the RNP to preserve or even increase activity and protect it from degradation. As such, the effect of chemical modifications on RNP assembly and activity must be known in detail. Importantly, the present disclosure shows that chemical modifications can tune the CRISPR/Cas9 RNP, resulting in enhanced activity and minimization of undesirable properties.

The present disclosure shows that chemical modification or substitution of RNA nucleotides in the CRISPR RNA (crRNA) or trans-acting CRISPR RNA (tracrRNA) portions of the enzyme can confer novel properties. These include significantly enhanced rates of target DNA cleavage, higher binding affinity of Cas9 for the crRNA, resulting in more efficient RNP assembly, greater specificity for desired targets, and crRNAs or tracrRNAs that contain little or no RNA bases for greater nuclease resistance. Specific modifications and their configuration in the crRNA or tracrRNA are required to achieve these results. Modifications that preserve the A-form helical structure of the crRNA, including, but not limited to, 2'-fluorinated nucleotides, in the crRNA "guide region," especially in the crRNA "seed region," are shown to retain cleavage activity. Modifications that enhance flexibility, specifically DNA bases and DNA analogs or mimics, including, but not limited to, 2'-fluoro-arabinonucleic acid (FANA), in the "tracrRNA-interacting region" of the crRNA enhance target DNA cleavage activity and RNP assembly. While not wishing to be limited to any one theory of the mechanism, enhanced cleavage and RNP assembly appear to be a result of forcing the Cas9 enzyme to prefer a catalytically competent structural state. The inventors have discovered mechanistic rules for applying chemical modifications to crRNAs and tracrRNAs that result in predictable tuning of the CRISPR/Cas9 RNP properties, as disclosed in greater detail herein below.

Methods of Using the Presently Disclosed Compositions

Applications for the findings disclosed herein include gene therapy, capture of DNA or targeting of Cas9 to DNA without causing cleavage, more rapid and precise genome editing, transfection of in vitro assembled CRISPR/Cas9 complexes for genome editing of cells and organisms in the laboratory, and any applications or biotechnology that would benefit from nuclease-resistant crRNA or enhanced assembly and cleavage kinetics of CRISPR/Cas9 RNP.

For therapeutics, one application involves delivering the Cas9 and tracrRNA via a virus, which can assemble inactive complexes inside of cells. The crRNA can then be administered later to assemble and selectively activate CRISPR/Cas9 RNP complexes, which would then go on to target and edit specific sites in the human genome, such as disease relevant genes (Gagnon and Corey, *Proc. Natl. Acad. Sci. USA* 112:15536-15537, 2015; Randar, et al., *Proc. Natl. Acad. Sci. USA* 112:E7110-7117, 2015). For this gene therapy approach to work the crRNA should be extremely resistant to nucleases and cellular degradation, as well as confer high activity and specificity to the assembled CRISPR/Cas9 RNP, both of which are properties of the presently disclosed compositions, for example crRNA_J.

Catalytically inactive Cas9, called dead Cas9 (dCas9), that has mutated catalytic residues is often used to bind Cas9 variants to double-stranded DNA as a laboratory tool (Du and Qi, "Cold Spring Harbor Protocols," pdb prot090175, 2016). In these types of experiments the tethered Cas9 can perform many functions, including activation or inhibition of transcription. As disclosed herein crRNAs composed of DNA or otherwise modified have been identified that can assemble stable RNP complexes but not cleave the targeted double-stranded DNA. These CRISPR/Cas9 RNPs allow use of normal catalytically competent Cas9 without the need to generate dCas9 mutants. This might be particularly useful in cases where a single Cas9 is expressed inside of cells but researchers would like to direct Cas9 to cleave some targets while only binding to other targets. Likewise, dCas9 can also be used as a tool to bind DNA of specific sequence and isolate, or capture, that DNA (O'Geen, et al., *Nucl. Acids Res.* 43:3389-3404, 2015). The use of crRNAs containing DNA or chemical modifications that block cleavage but still allow binding are particularly useful as an alternative approach to dCas9. Finally, combining the presently described modified crRNAs with dCas9 has benefits that improve DNA capture since the crRNA is more resistant to nucleases.

The present disclosure describes modified crRNAs, such as crRNA_J configurations, that form CRISPR/Cas9 complexes with enhanced catalytic activity but that retain sequence specificity. CRISPR/Cas9 with enhanced cleavage activity results in faster and more efficient editing of genomic DNA inside of cells. In particular, chemically modified crRNAs with high nuclease resistance also result in more persistent editing. The present results showing that crRNA_J configurations confer strong discrimination against mismatched bases result in even more precise gene editing with fewer off-target effects. Altogether these findings improve the efficiency and precision of genome editing. This shortens the time needed to generate successfully edited cells for laboratory research or improve the safety of CRISPR/Cas9 for therapeutic applications.

Currently CRISPR/Cas9 complexes can be assembled in vitro and directly transfected into cells for genome editing (Liang, et al., *J. Biotechnol.* 208:44-53, 2015; Zuris, et al., *Nat. Biotechnol.* 33:73-80, 2015). This approach has been commercialized by companies like IDT and special transfection reagents, such as CRISPRMAX (Yu, et al., *Biotechnol. Lett.* 38:919-929, 2016), have been developed for this purpose. The presently disclosed chemically modified crRNAs substantially improve this approach by offering superior stability against degradation, enhanced catalytic activity, and greater discrimination against mismatched targets.

A number of applications benefit from chemically stabilized crRNAs or CRISPR/Cas9 RNP complexes with enhanced cleavage rates. The number of applications range from therapeutic approaches and human gene therapy to molecular laboratory tools and topical antimicrobials in hospital settings.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Recombinant Cas9 Protein Expression and Purification

The pET-Cas9-NLS-6xHis plasmid (62933) containing the gene encoding Cas9 from *S. pyogenes* with a C-terminal nuclear localization signal (NLS) and 6× histidine tag was purchased from Addgene (Cambridge, Mass.) (Zuris, et al., 2015, supra). Plasmid was transformed into Rosetta (DE3) *E. coli* and Cas9 protein expressed and purified similarly to that described previously (Anders and Jinek, *Methods Enzymol.* 546, 1-20, 2014). Briefly, cells were grown to an optical density of 0.6 in LB broth containing 100 µg/mL carbenecillin, then moved to 18° C. and expression of Cas9 induced by addition of 0.2 mM IPTG for 24 h. Cells were then collected by centrifugation, resuspended in lysis buffer (20 mM Tris, pH 8, 0.25 M NaCl, 5 mM imidazole, 1 mM PMSF), sonicated, then the lysate clarified by centrifugation. Soluble protein was poured over a cobalt-CMA affinity chromatography resin column and washed with 20 bed volumes of wash buffer (20 mM Tris, pH 8, 0.5 M NaCl, 10 mM imidazole, 0.05% Tween-20). Protein was eluted from the column with 3 bed volumes of elution buffer (20 mM Tris, pH 8, 0.25 M NaCl, 150 mM imidazole), concentrated, then dialyzed against dialysis buffer (20 mM Tris, pH 7.5, 125 mM KCl, 10% (v/v) glycerol, 1 mM EDTA). Protein concentration was determined by UV absorbance at 280 mu and using Beer's law. Protein was diluted to 10 mg/mL in dialysis buffer, aliquoted and stored at −80° C.

To make the dead Cas9 (dCas9) protein mutant, site-directed mutagenesis was used to make D10A and H840A mutants. The dCas9 protein was purified exactly the same as described for regular Cas9 described above.

Example 2

In Vitro Transcription of sgRNA and tracrRNA

RNA was transcribed and purified as previously described (Ageely, et al., *ACS Chem. Biol.* 11:2398-2406, 2016). Briefly, a DNA template containing the T7 promoter sequence and the sequence to be transcribed was purchased from Integrated DNA Technologies (IDT; Coralville, Iowa). The DNA template was annealed to a T7 promoter oligo to prepare a double-stranded DNA template at the promoter sequence. Template was used for in vitro transcription by T7 RNA polymerase. After DNase treatment and phenol extraction, RNA was then purified by resolving on denaturing polyacrylamide gels containing 1× TBE and 7 M urea. RNA bands were lightly stained with methylene blue in water and then extracted and eluted by crush and soak elution. RNA was precipitated, resuspended in 5 mM Tris, pH 7.2, 0.1 mM EDTA and its concentration determined using UV absorbance at 260 nm and Beer's law with calculated extinction coefficients.

Example 3

CRISPR/Cas9 in Vitro Cleavage Assays

Cleavage assays were performed similarly to that published previously (Anders and Jinek, 2014, supra). Plasmids used were a custom EGFP-containing plasmid (pIDT-SMART-EGFP) purchased from IDT and pcDNA6/TR (Life Technologies, Carlsbad, Calif.), which contains the tetracycline repressor gene. These plasmids were linearized with restriction enzymes prior to cleavage assays. Cleavage reactions contained a final of 250 nM tracrRNA, 300 nM crRNA, 750 nM Cas9, 0.1 µg/µL tRNA, and 220 ng of linearized plasmid or 1.3 pmol of FAM-duplex DNA in 40 µL of 1× cleavage buffer (20 mM Tris, pH 7.5, 100 mM KCl, 5% glycerol, 1 mM DTT, 0.5 mM EDTA, 2 mM $MgCl_2$). Reactions were typically incubated at 37° C. for 2 h unless otherwise noted. To each reaction 1 µL of RNase A (10 mg/mL) was added and incubation continued for 15 min at room temperature. Then 1 µL of Proteinase K (20 mg/mL) was added and incubated for another 15 min at room temperature. Reactions were stopped and precipitated by adding 360 µL of 2% $LiClO_4$ in acetone and incubating at −20° C. for 1 h or more. DNA was pelleted by centrifugation, washed 1× with acetone, then the dry pellet was resuspended in native loading dye (1× TBE, 10% glycerol, orange G dye) and resolved on either a TBE agarose gel (plasmid) or a TBE acrylamide gel (FAM target). Bands were visualized by ethidium bromide staining (plasmid) or scanning in a Typhoon laser imager (FAM target). Cleavage efficiency was quantified using ImageJ software.

Example 4

Dot Blot Assays

Dot blot assays were used to measure binding of a preformed Cas9-tracrRNA complex to various crRNAs. Cas9-tracrRNA complexes were assembled as described above for CRISPR/Cas9 cleavage assays except the crRNA was omitted and it also contained BSA at a final concentration of 0.25 mg/mL. This reaction was then serially diluted into 1× cleavage buffer containing 0.1 mg/mL tRNA and 0.25 mg/mL BSA. Assembled Cas9-tracrRNA complexes were mixed with 1500 cpms of 5'-radiolabeled and gel-purified crRNA, corresponding to 2-5 nM of radiolabeled crRNA, for each binding reaction. Reactions were then incubated at 37° C. for 15 min then spotted to nitrocellulose membrane in a 96-well dot blot apparatus and washed 2× with 200 µL of 1× cleavage buffer. The membrane was then removed from the dot blot apparatus and washed three additional times in 1× cleavage buffer, then dried and exposed to a phosphorimager screen overnight. Spots were quantified by ImageJ, binding curves plotted in Prism, and $K_d$ values predicted by nonlinear regression and a one-site hyperbolic binding fit in Prism. Binding of a fully assembled CRISPR/Cas9 RNP to radiolabeled duplex DNA was essentially carried out in the same manner and with the same buffers and conditions, except binding was to a duplex DNA oligonucleotide.

Example 5

Electrophoretic Mobility Shift Assays (Gel Shifts)

To observe assembly of CRISPR/Cas9 RNP complexes, tracrRNA was 5'-radiolabeled and gel-purified. Binding reactions were performed under similar conditions used for Cas9 cleavage assays. Cas9 was first serially diluted into 1× dialysis buffer then mixed with 5000 cpm of tracrRNA, 0.5 µg/µL tRNA, 0.5 µg/µL BSA, and 10 U of SUPERase-In (Ambion, Austin, Tex.) in 1× cleavage buffer in a final of 10 µL reaction volume. After incubation at 37° C. for 15 min, reactions were mixed with 4 µL of native loading dye (1× Tris-borate (TB), orange G, 40% glycerol) and resolved on a 5% native TB polyacrylamide gel. After electrophoresis, gels were dried and exposed to a phosphorimager screen overnight.

Example 6

Synthesis of Chemically Modified crRNAs

Standard phosphoramidite solid-phase synthesis conditions were used for the synthesis of all modified and unmodified oligonucleotides. Syntheses were performed on an Applied Biosystems 3400 or Expedite DNA Synthesizer at a 1-µmol scale using Unylink CPG support (ChemGenes, Wilmington, Mass.). All phosphoramidites were prepared as 0.15 M solutions in acetonitrile (ACN), except DNA, which was prepared as 0.1 M. Mixmer samples were prepared using premixed 1:1 equivalents of RNA 2'-amidite with RNA 3'-amidite (mix1), or 1:1 equivalents of RNA 2'-amidite or DNA 3'-amidite (mix2), or 1:1 equivalents of RNA 2'-amidite with 2'F-RNA 3'-amidite, 2'-F,4'-OMe-rU and 2',4'-diOMe-rU phosphoramidites were prepared as 0.15 M solutions in acetonitrile, 5-ethylthiotetrazole (0.25 M in ACN) was used as an activator. Detritylations were accomplished with 3% trichloroacetic acid in $CH_2Cl_2$ for 110 s. Capping of failure sequences was achieved with acetic anhydride in tetrahydrofuran (THF) and 16% N-methylimidazole in THF. Oxidation was done using 0.1 M $I_2$ in 1:2:10 pyridine:water:THF. Coupling times were 600 s for RNA, F-ANA, F-RNA, LNA (5-methyl-C and 5-methyl-T) phosphoramidites, 2'5', mix1 and mix2, and 2'-F,4'-OMe-rU and 2',4'-diOMe-rU, with the exception of the guanosine phosphoramidites which were allowed to couple for 900 s. Deprotection and cleavage from the solid support was accomplished with either 3:1 $NH_4OH$:EtOH for 48 h at room temperature (rt), or at 55° C. for 16 h. Oligonucleotides containing RNA were synthesized with standard 2'-TBDMS phosphoramidites, and desilylation was achieved with either neat triethylamine trihydrofluoride for 48 h at rt, or with triethylamine trihydrofluoride/N-methyl pyrrolidone/triethylamine (1.5:0.75:1 by volume) for 2.5 h at 65° C. Crude oligonucleotides were purified by anion exchange HPLC on an Agilent 1200 Series Instrument using a Protein-Pak DEAE 5PW column (7.5×75 mm) at a flow rate of 1 ml/min. The gradient was 0-24% of 1 M lithium perchlorate over 30 min at 60° C. Under these conditions, the desired peaks eluted at roughly 23-27 minutes. Samples were desalted on NAP-25 desalting columns according to manufacturer protocol.

Example 7

CRISPR/Cas9 Elements

The natural CRISPR/Cas9 RNP is composed of one protein, Cas9, and two RNA molecules, the CRISPR RNA (crRNA) and the trans-acting crRNA (tracrRNA) (Sander and Joung, *Nat. Biotechnol.* 32:347-355, 2014). The two RNA components can also be made as an artificial fusion called a single guide RNA (sgRNA). CRISPR/Cas9 can enzymatically cleave, or cut, a double-stranded DNA by breaking a specific phosphodiester bond when its guide region (part of the crRNA sequence) is perfectly complementary to the DNA sequence (FIG. 1A).

To setup CRISPR/Cas9 experiments, the Cas9 protein derived from *Streptococcus pyogenes* was expressed in Rosetta (DE3) *E. Coli* cells from a publically available plasmid purchased from Addgene following standard purification procedures (Anders and Jinek, 2014, supra). This particular Cas9 enzyme contains a C-terminal nuclear localization signal (NLS) and a 6× histidine tag for affinity purification (Zuris, et al., 2015, supra). Tags were not removed after purification. The tracrRNA was made enzymatically by in vitro transcription and unmodified crRNAs were purchased as chemically synthesized nucleic acids from IDT.

To establish an assay for testing chemical modification of the crRNA, it was decided to target EGFP, a common gene used in many laboratories. A restriction enzyme was used to linearize a plasmid that contains the EGFP coding sequence so that successful cleavage by a CRISPR/Cas9 enzyme would result in two new product bands on a gel when the reaction was resolved by gel electrophoresis (FIG. 1B). A synthetic double-stranded (duplex) DNA that contains the EGFP target sequence was purchased. The antisense strand of the duplex contains a 3' fluorescein (FAM) tag to enable visualization of the cleavage products by fluorescence imaging (FIG. 1C).

Conditions for efficient cleavage of either the linearized EGFP plasmid or the artificial FAM-labeled duplex DNA was established. Then crRNAs were synthesized that contained substitutions of DNA in place of RNA throughout the crRNA. The crRNA has two main functional regions within it. One is a 20 nucleotide guide region at the 5' end of the crRNA, which base-pairs with the target DNA (FIG. 1D). Contained within the guide region at one end there is a smaller 8-9 nucleotide seed sequence, which is critical for seeding, or initiating, the hybridization to the DNA target (Nishimasu, et al., *Cell* 156, 935-949, 2014). The second part is the tracrRNA-interaction region, which base-pairs with the tracrRNA as part of the RNP assembly process (Jiang, et al., *Science* 348, 1477-1481, 2015). The tracrRNA-interaction region is 22 nucleotides long and is found at the 3' end of the crRNA (FIG. 1D).

Example 8

Chimeric CRISPR/Cas9 Structures and Cleavage Results

Figure 2:
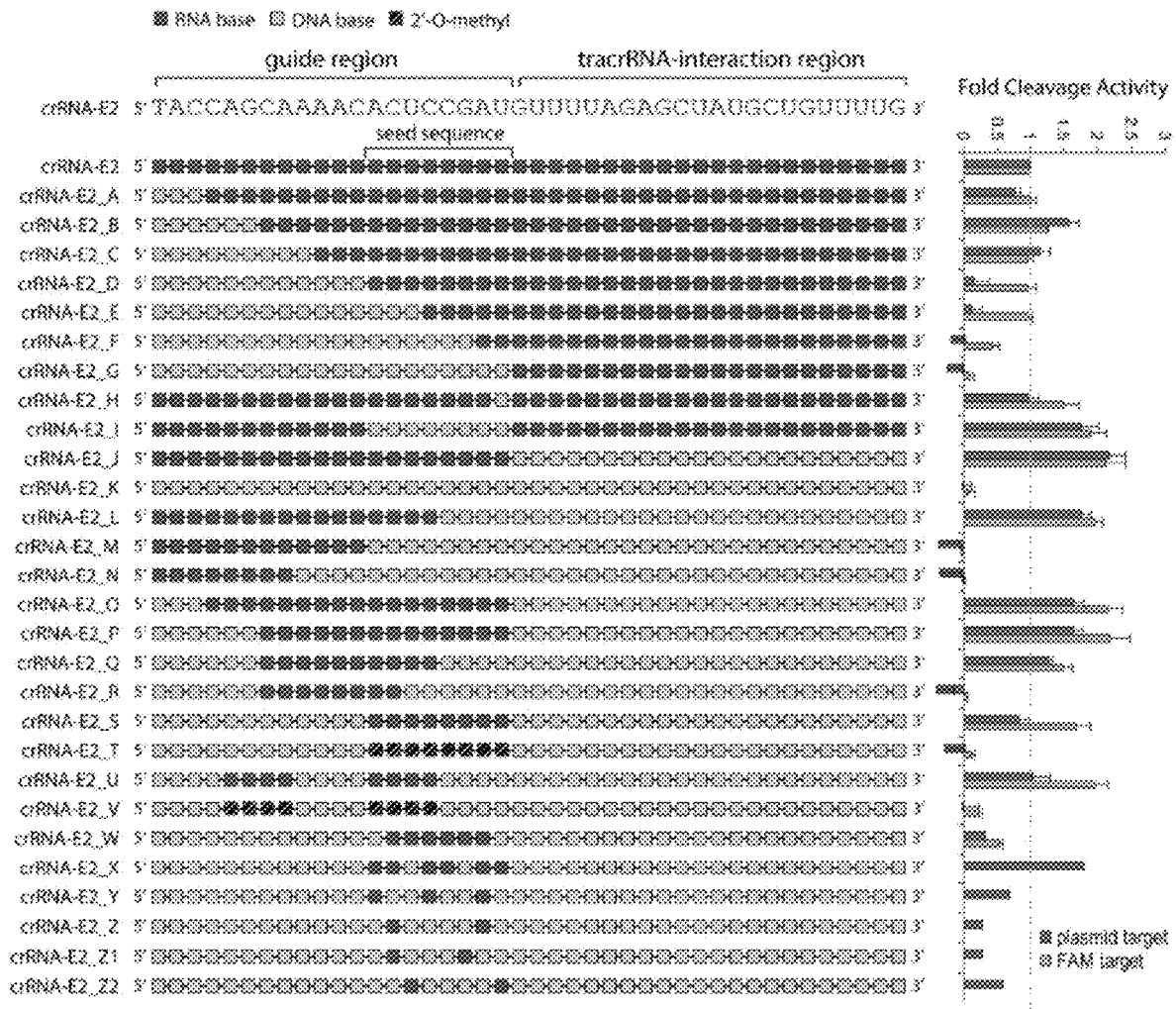
FIG. 2 shows RNA-DNA chimeras of crRNA-E2. RNA, DNA, and 2'-O-methyl nucleotides are shown as orange, blue, and red squares, respectively. Corresponding cleavage activities for CRISPR/Cas9 RNP complexes assembled from each crRNA on plasmid DNA (purple) or FAM-duplex DNA (green) are shown to the right.

The RNA-DNA chimeras of crRNA that were tested revealed a variety of activities (FIG. 2). Several notable trends emerged. First, replacing RNA bases with DNA in the guide region, starting at the 5' end, was detrimental to activity. In contrast, replacing the RNA bases with DNA in the tracrRNA-interaction region significantly enhanced cleavage. Combinations of substitutions confirmed this general trend. Attempting to replace remaining RNA bases with 2'-O-methyl for some RNA-DNA chimeras resulted in total loss of cleavage activity, highlighting a unique aspect of RNA bases with 2'-hydroxyl groups. In addition, attempting to minimize the number of RNA bases in the guide region resulted in chimeras that retained activity with as little as 2 RNA bases, with 6-8 RNA bases being the minimum to retain similar activity to that of an all-RNA crRNA. Importantly, minimizations of RNA base content revealed that RNA bases should be within or overlapping the seed sequence of the crRNA.

Example 9

Cleavage Activity of crRNA-E2_J

Figure 3A:
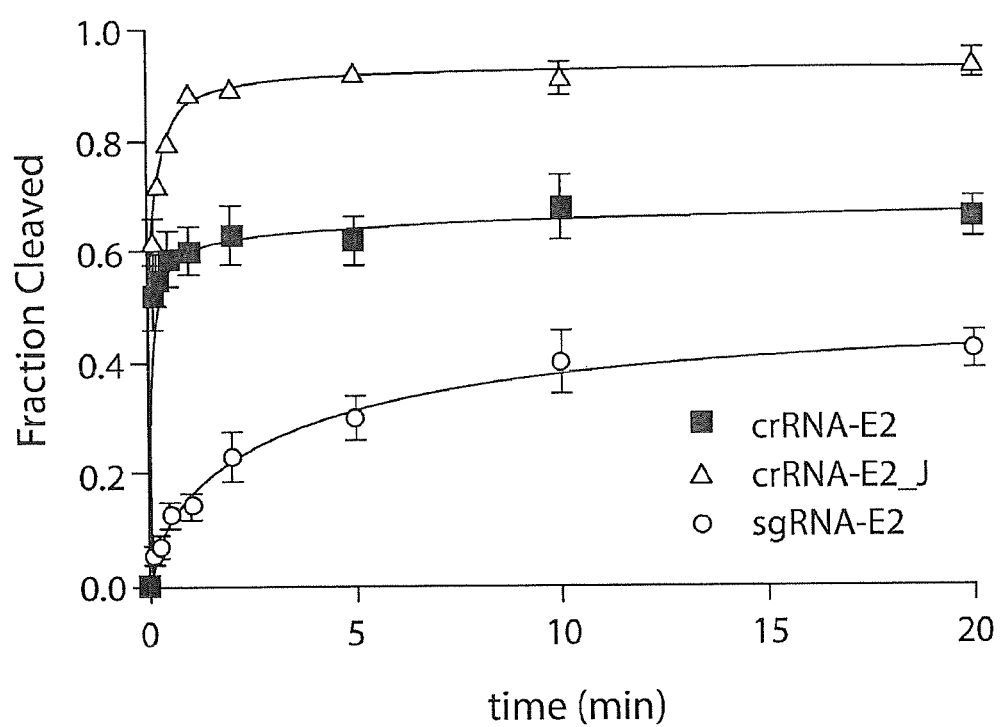
FIG. 3A and FIG. 3B show cleavage activity of crRNA-E2, crRNA-E2_J and sgRNA-E2.
Figures 3B, 3C:
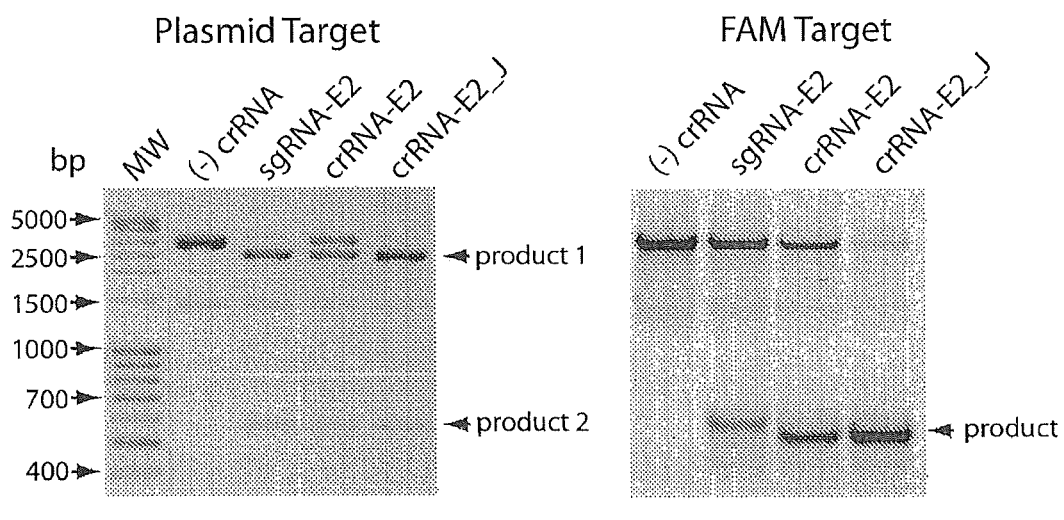
FIG. 3C is a comparison of crRNA-E2_J cleavage of FAM duplex DNA with sgRNA-E2 and crRNA-E2 targeting the same sequence.

The most active crRNA chimera configuration was crRNA-E2_J, which contained all RNA bases in the guide region and all DNA bases in the tracrRNA-interaction region. crRNA-E2_J was found to significantly enhance the rate of target DNA cleavage compared to crRNA-E2 and sgRNA-E2 as determined by a time-course experiment (FIG. 3A). It increased the total amount of DNA cleavage by approximately 3-fold. crRNA-E2_J performed very similar to a sgRNA targeting the same EGFP site on a plasmid (FIG. 3B) and outperformed a sgRNA when targeting a FAM-labeled duplex DNA target (FIG. 3C). Chimeric crRNAs that had the highest activity maintained a substitution pattern similar to or overlapping with the crRNA-E2_J configuration.

Example 10

Cleavage Activity of Shortened Versions of crRNA-E2_J and Modified tracrRNA

Figure 4A:
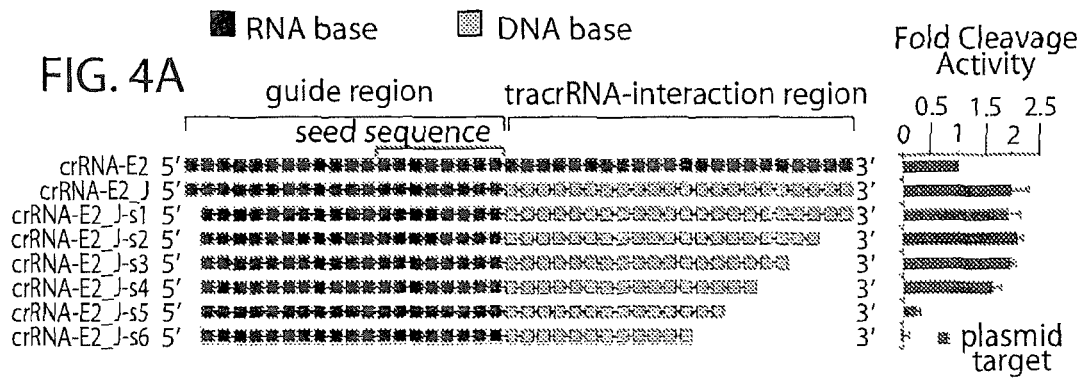
FIG. 4A, FIG. 4B and FIG. 4C show cleavage activity of shortened versions of crRNA-E2_J and cleavage activity of tracrRNA with DNA nucleotide substitutions.
Figure 4B:
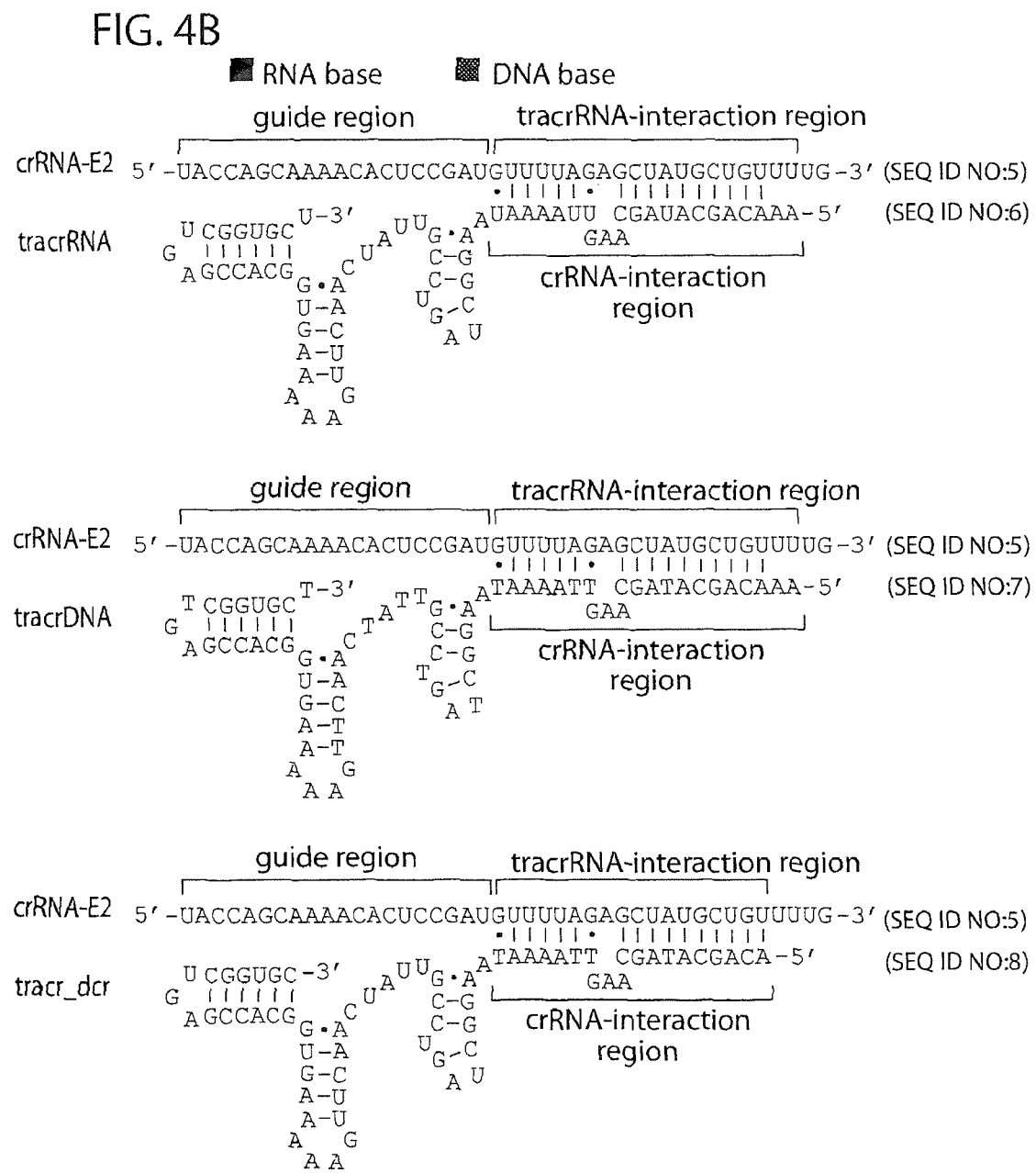
Figure 4B:
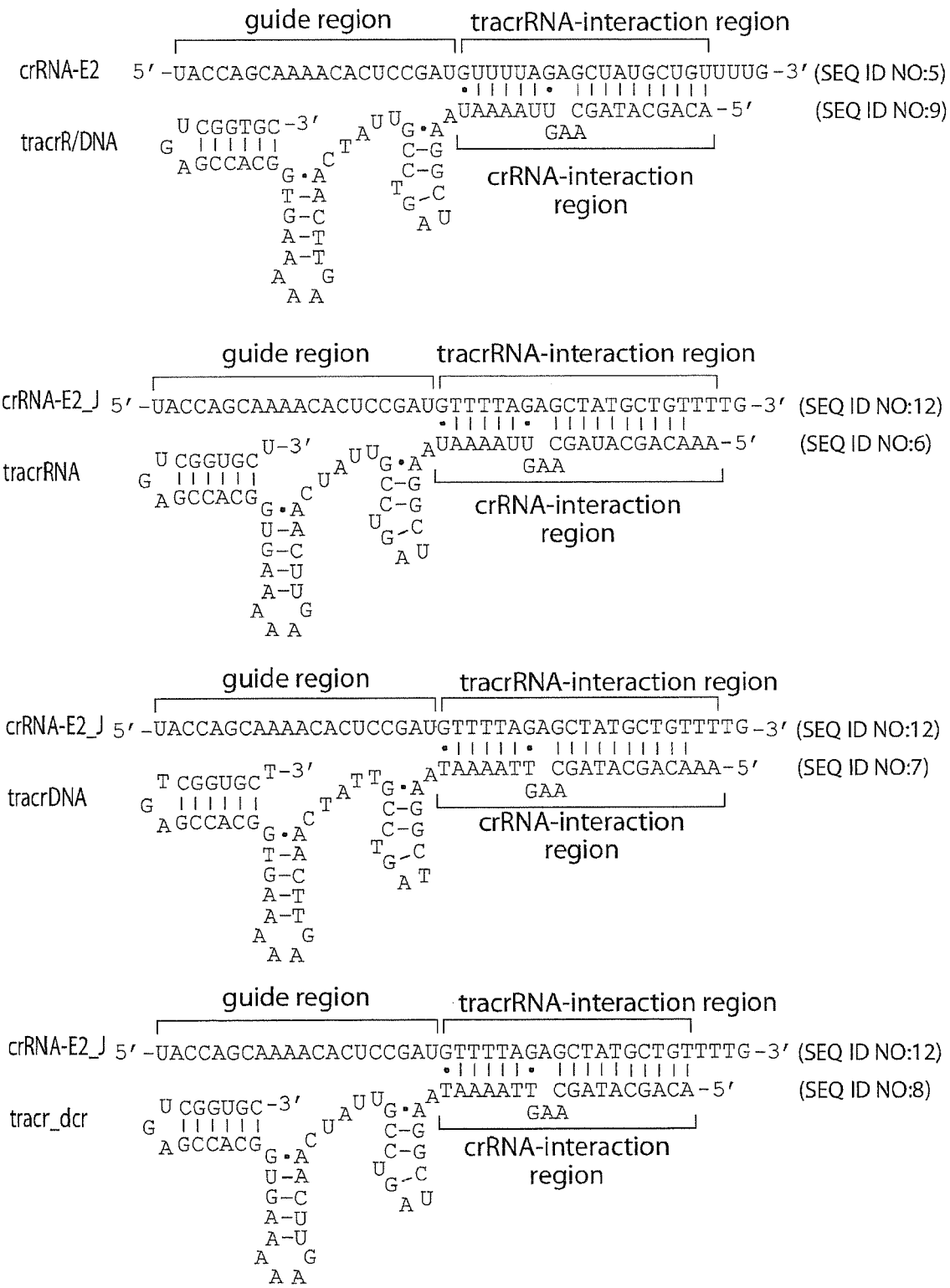
Figure 4B:
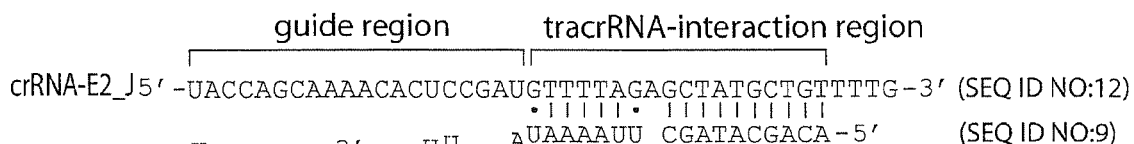
Figure 4B:
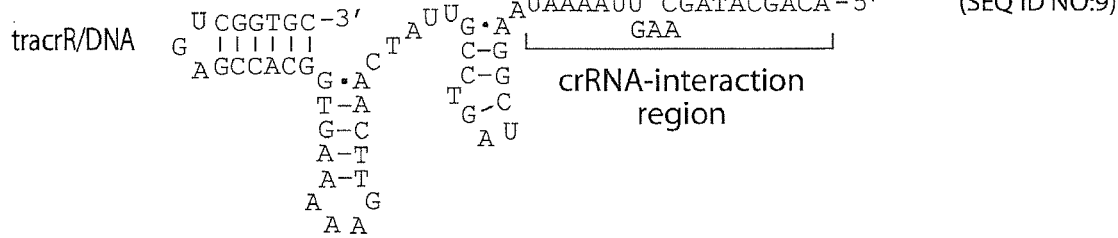
Figure 4B:
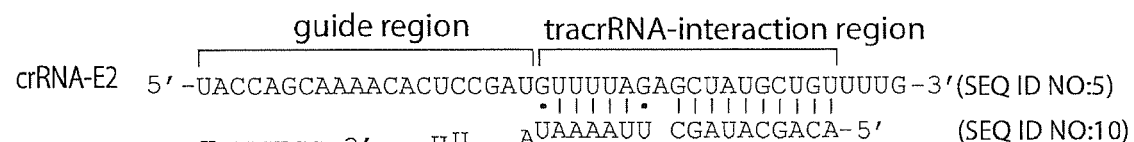
Figure 4B:
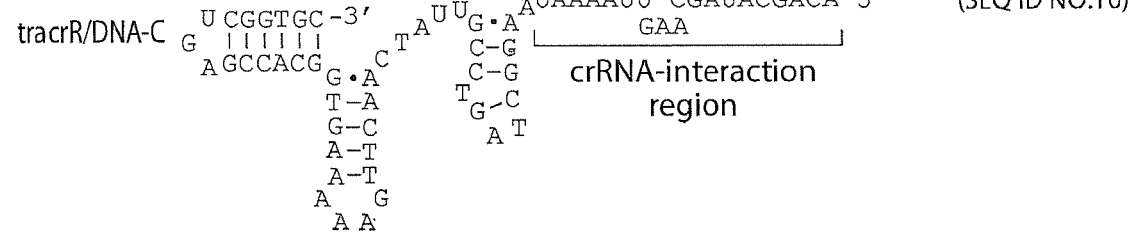
Figure 4B:
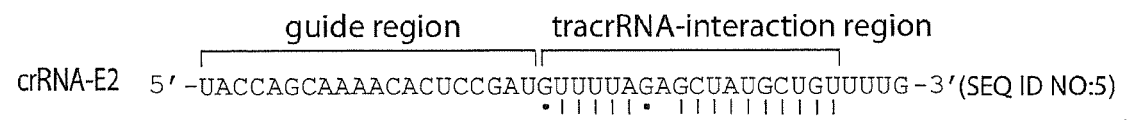
Figure 4B:
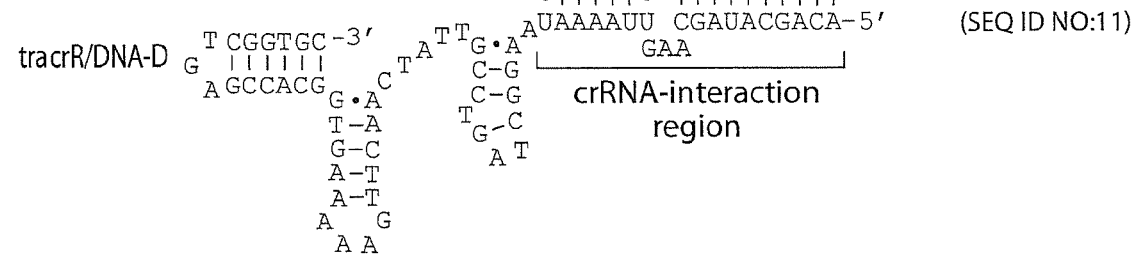
Figure 4B:
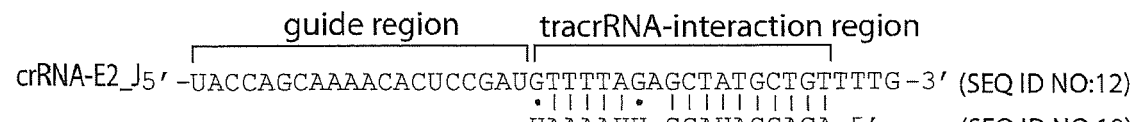
Figure 4B:
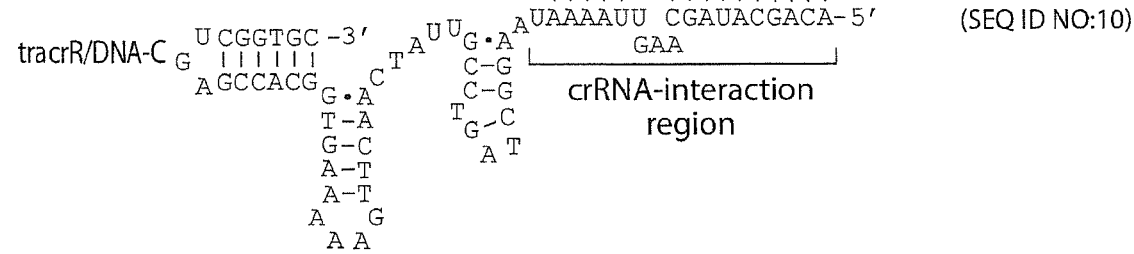
Figure 4B:
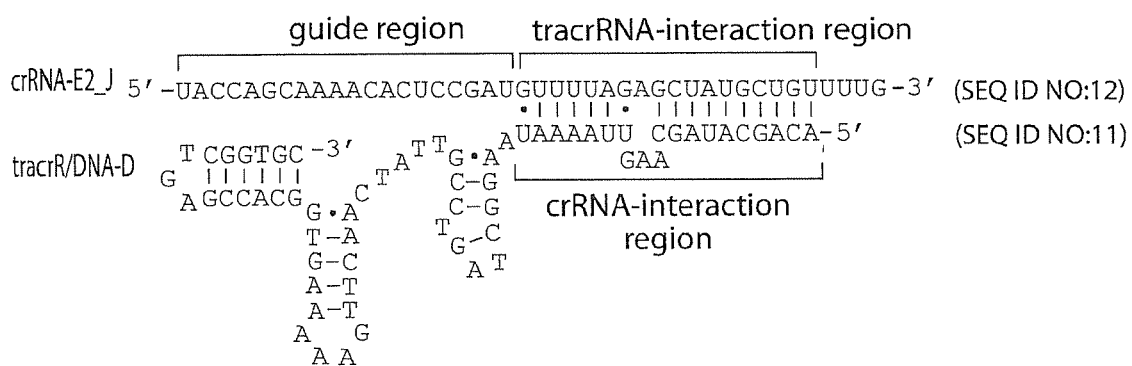
Figure 4C:
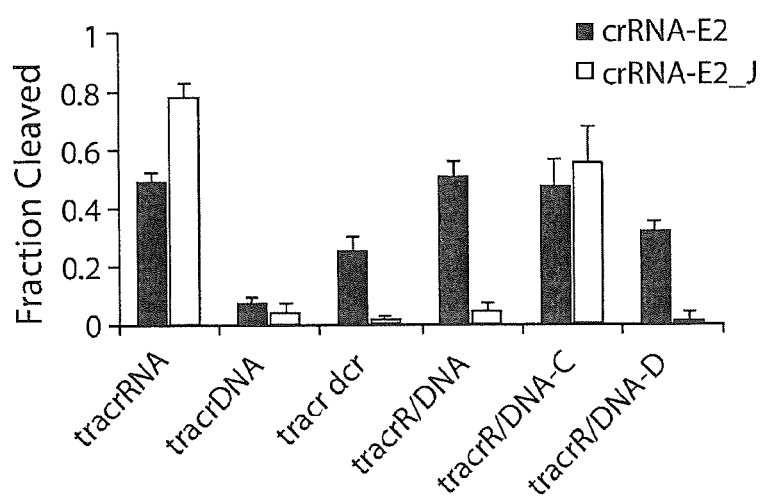

Shortened versions of crRNA-E2_J were also tested (FIG. 4A). It was found that one base could be removed from the 5' end and 6 bases removed from the 3' end and still retain similar activity to that of the original crRNA-E2_J. Because crRNA-E2_J possessed DNA in its tracrRNA-interaction region, switch experiments were prepared where crRNA:tracrRNA RNA-DNA swap mutants were made (FIG. 4B). When assembled with Cas9 and either an all-RNA crRNA-E2 or crRNA-E2_J, the tracrR/DNA-C swap mutant showed similar activity, albeit slightly reduced, to an all-RNA tracrRNA. Interestingly, combining an all-DNA tracrRNA with either of the crRNAs resulted in no activity. The other tracrR/DNA swap mutants (dcr, DNA and DNA-D) resulted in some activity with the all-RNA crRNA-E2, but this activity was lost with crRNA-E2_J. Thus, maintaining RNA in one strand of the tracr-crRNA interaction duplex retains cleavage activity and replacing RNA with DNA in the tracrRNA-interaction region of the crRNA is the most beneficial for activity.

Example 11

Cleavage Activity for crRNAs Targeting Different DNA Sequences

Figure 5A:
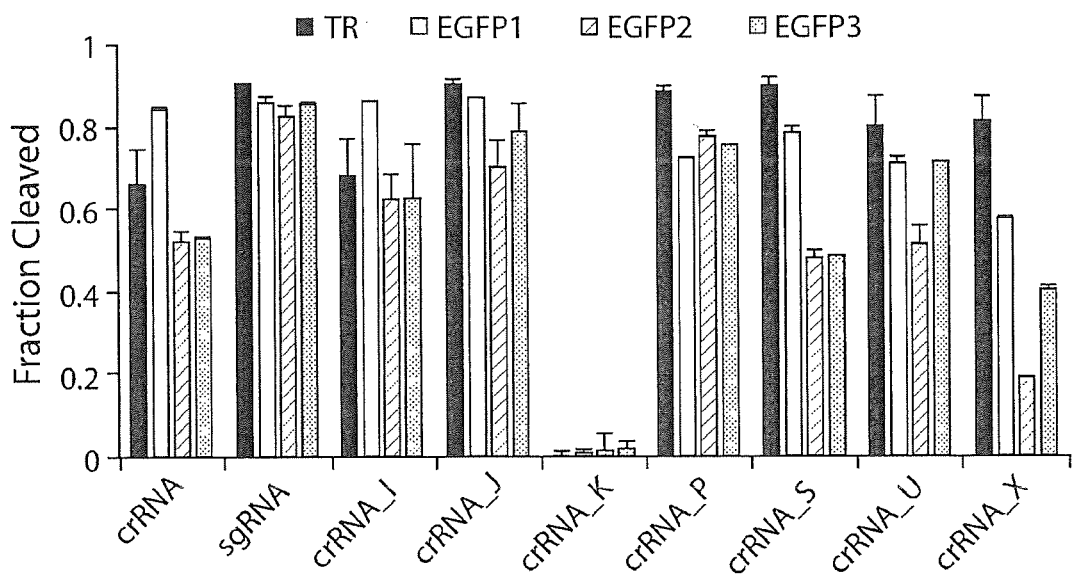
FIG. 5A and FIG. 5B show a comparison of cleavage activity for crRNAs targeting different DNA sequences and cleavage activity using an Cas9 from *Staphylococcus aureus* (SaCas9).

To determine the generality of these findings, new crRNAs were designed with different guide sequences that targeted three different regions of the EGFP plasmid and the tetracycline repressor (TR) gene (FIG. 5A). Using the same plasmid cleavage assay as before, it was found that crRNA_J, crRNA_J, crRNA_P, crRNA_S, crRNA_U and crRNA_X performed nearly as well or better than the crRNA or the sgRNA. Only crRNA_K was inactive.

Example 12

Cleavage Activity Using an Cas9 from Staphylococcus Aureus

Figure 5B:
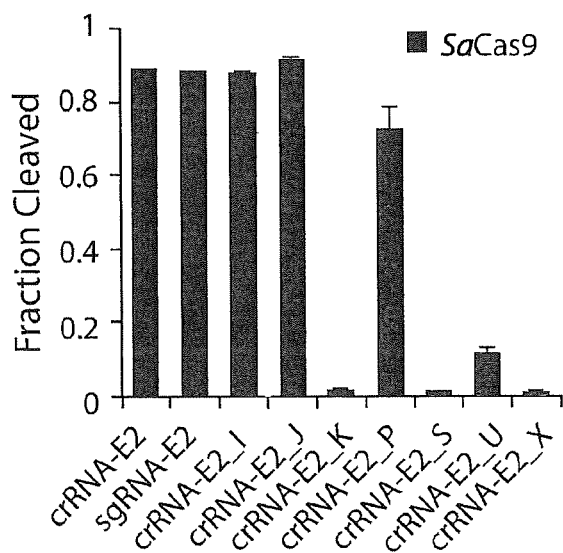

To determine if the DNA-substituted crRNAs are compatible with cleavage activity when using sources of Cas9 other than from *Streptococcus pyogenes*, the cleavage activity of the DNA-substituted crRNAs were analyzed using Cas9 from *Staphylococcus aureus* (SaCas9; FIG. 5B). The results show that most of the DNA-substituted crRNAs tested have cleavage activity similar to Cas9 from *Streptococcus pyogenes* when using SaCas9, suggesting that other sources of Cas9 can be used with most of the DNA-substituted crRNAs disclosed herein.

Example 13

Cleavage Specificity of crRNA-E2_J

Figure 6A:
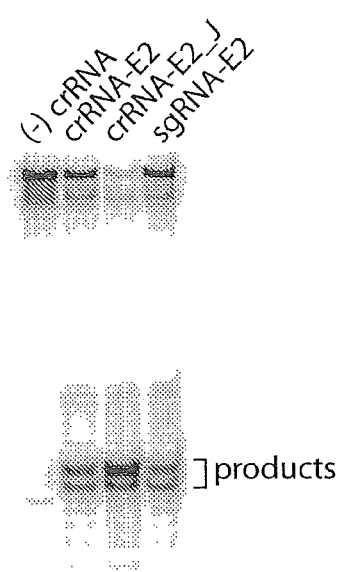
FIG. 6A and FIG. 6B show cleavage specificity of crRNA-E2_J.
Figure 6B:
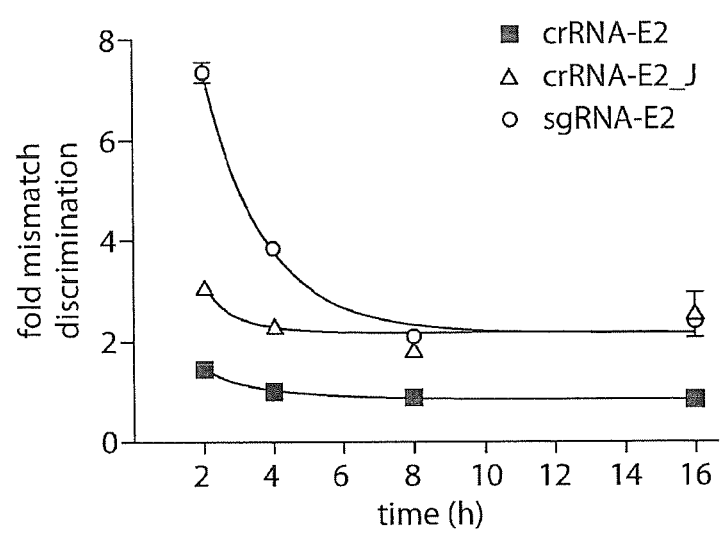

Because crRNA_J versions and other similar chimeras seem to confer accelerated kinetics on the enzyme, the specificity of the CRISPR/Cas9 RNP complexes that contain chimeric crRNAs was also tested. Enzymes that work faster can sometimes become less specific. In the case of nucleases, this might result in cleavage of unintended phosphodiester bonds between nucleotides. A standard cleavage assay was performed using duplex DNA as a target, but instead radiolabeled the antisense strand for stronger signal during visualization of the gel. Cleavage products were then resolved on a high resolution sequencing gel that can provide single nucleotide resolution. As previously observed, crRNA-E2_J provided more robust cleavage activity. However, no differences in the cleavage pattern were observed for crRNA-E2_J as compared to the all-RNA crRNA-E2 and a sgRNA-E2 (FIG. 6A), indicating that site-specific cleavage is not compromised by the accelerated activity of crRNA-E2_J. To further investigate target specificity, a mismatch FAM-labeled duplex DNA was prepared with a single C to G mutation at the 5th position of the seed sequence (from the 3' end), generating a G:G mismatch near the center of the seed sequence when paired with a crRNA-E2 guide. CRISPR/Cas9 complexes assembled from crRNA-E2, crRNA-E2_J, and sgRNA-E2 were incubated with either perfect match or mismatch targets for 16 h, 8 times the usual assay time. For the perfect match target the usual cleavage efficiencies were observed, despite an extended incubation time. Comparing the change in cleavage of crRNA-E2_J with respect to crRNA-E2 for the mismatch target revealed a 2-fold difference in cleavage, similar to that observed for sgRNA-E2 (FIG. 6B). Thus, in this case crRNA-E2_J is able to discriminate between a single nucleotide mismatch target and a perfect target sequence approximately 2 times better than the all-RNA crRNA-E2, which indicates significantly improved enzyme specificity.

Example 14

Figure 7A:
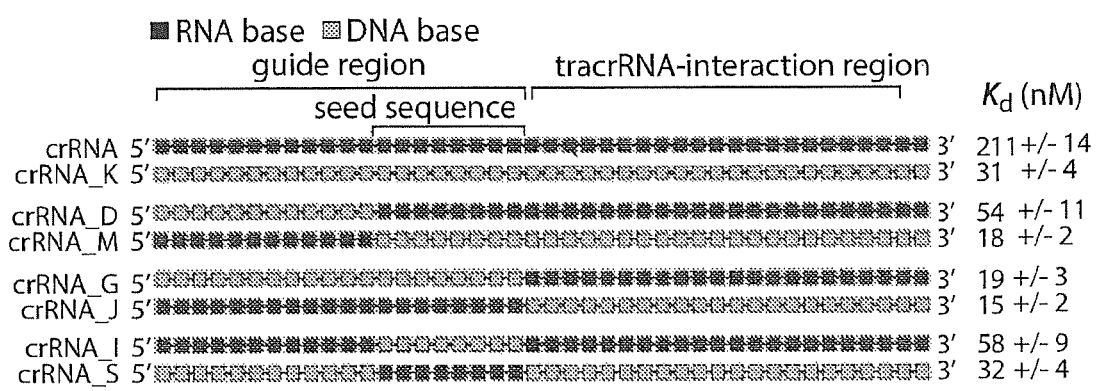
FIG. 7A, FIG. 7B and FIG. 7C show assembly and target DNA binding of CRISPR/Cas9 RNP complexes containing RNA-DNA chimeric crRNAs.
Figure 7B:
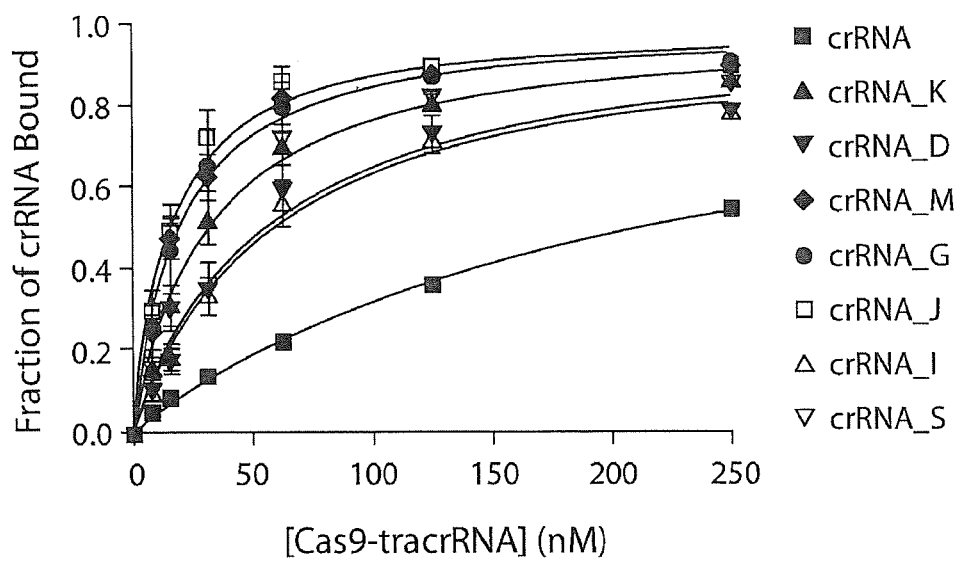

Assembly and Target DNA Binding of CRISPR/Cas9 RNP Complexes Containing RNA-DNA Chimeric crRNAs To better understand the effect of DNA substitution of crRNA on Cas9 activity, the assembly of the CRISPR/Cas9 RNP was studied using RNA-DNA chimeric crRNAs (FIG. 7A). Using a dot-blot technique, it was found that all of the DNA-containing crRNAs tested, with a variety of cleavage activities, bound to a pre-assembled Cas9-tracrRNA complex much tighter than an unmodified crRNA-E2 (FIG. 7B). Dissociation constants determined from these analyses (FIG. 7A, right) revealed a significant increase in the binding affinity of the DNA-containing crRNAs, with crRNA_J exhibiting over an order of magnitude increase in the binding affinity. Interestingly, an all-DNA crRNA, called crRNA-E2_K, showed very high binding affinity as well. However, crRNA-E2_K shows no cleavage activity and thus assembles an inactive CRISPR/Cas9 RNP complex. These results indicate that incorporation of DNA nucleotides into the crRNA generally improves assembly of CRISPR/Cas9 RNP complexes.

Figure 7C:
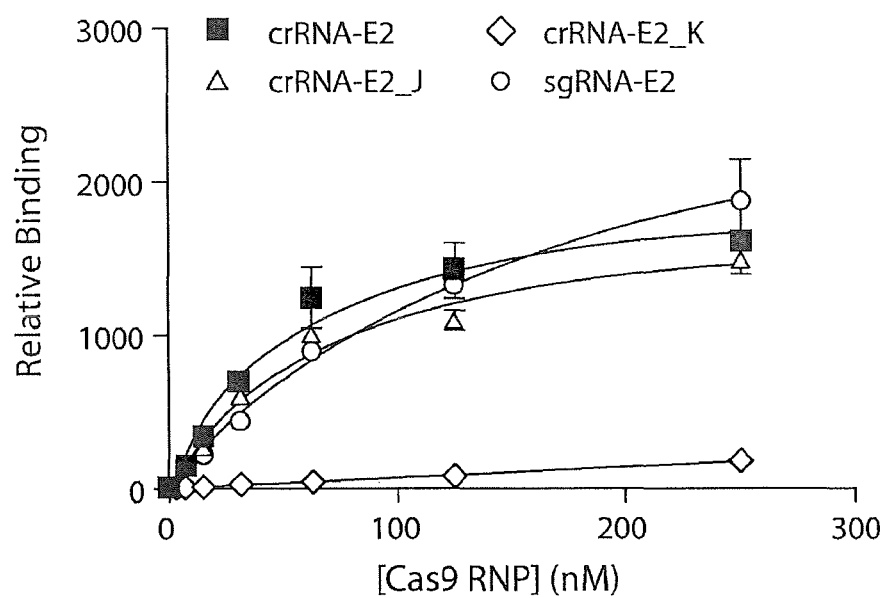

The ability of RNA-DNA chimeric CRISPR/Cas9 RNP complexes to bind and engage a duplex DNA substrate was also studied. DeadCas9 was used in these studies so the duplex DNA would not be cleaved. Results comparing all-RNA crRNA-E2, all-RNA sgRNA-E2 and crRNA-E2_J showed no appreciable difference in the binding properties toward the target DNA, but crRNA-E2_K showed a significant difference (FIG. 7C). A sgRNA is considered a superior design because it facilitates better assembly of the CRISPR/Cas9 RNP and also shows much higher cleavage activity than a three-component Cas9 RNP assembled from tracrRNA, crRNA and Cas9 (Sander and Joung, 2014, supra). Thus, these results suggest that target binding is unlikely to explain the enhanced cleavage activity of crRNA-E2_J and other DNA-containing crRNAs since CRISPR/Cas9 complexes assembled from a crRNA and tracrRNA perform similarly to those assembled from sgRNA.

Example 15

Mobility Shift Assays

Figure 8:
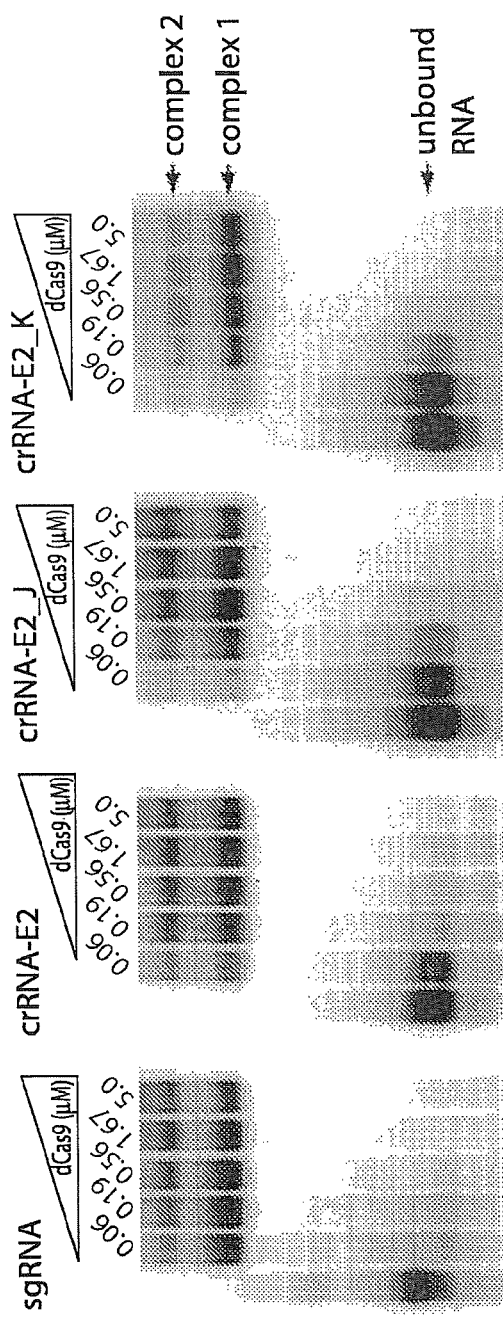
FIG. 8 shows electrophoretic mobility shift assays of radiolabeled tracrRNA binding with crRNA and Cas9. sgRNA and crRNA-E2 assemble into two complexes, complex 1 and 2. crRNA-E2_J preferentially forms complex 2 while crRNA-E2_K preferentially forms complex 1.

The CRISPR/Cas9 complex was recently shown to possess two structural states after assembling into an RNP complex and two structural states after binding to a target DNA substrate (Jiang, et al., *Science* 351:867-871, 2016; Sternberg, et al., *Nature* 527:110-113, 2015). In both cases, one structural state is "active" and competent for inducing cleavage while the other state is "inactive" or incapable of inducing cleavage. To determine if crRNA-E2_J may be favoring the active state versus the inactive state of the enzyme, the tracrRNA component was radiolabeled and then crRNA and Cas9 were added to the reaction. Assembled RNP complexes were then resolved on a native polyacrylamide gel to preserve their natural shape and structure. This method revealed that the Cas9 RNP appears to assemble into two structural states that run as a lower (complex 1) and upper (complex 2) band on the gel (FIG. 8). The sgRNA and all-RNA crRNA-E2 separated approximately equally into upper and lower bands. The crRNA-E2_J assembled primarily into a complex that ran as an upper band. In contrast, crRNA-E2_K assembled primarily into a complex that ran as a lower band. Notably, the distribution of these different complexes into upper and lower bands corresponds with their relative cleavage activity, suggesting that the upper band represents the catalytically-competent state while the lower band is an inactive complex.

Example 16

Studies on crRNAs Comprising Chemically Modified RNA and DNA Nucleotides

The presence of only a few RNA bases can force an A-form helical structure on that local region of a nucleic acid (Wahl and Sundaralingam, *Nucl. Acids Res.* 28:4356-4363, 2000). This is because of steric constraints introduced by the 2'-hydroxyl on the ribose ring of RNA nucleotides. In contrast, DNA lacks a 2'-hydroxyl and is therefore considered more flexible. When base-paired to RNA or when containing enough RNA bases, the resulting hybrid will prefer A-form or A-form-like helical structure (Bachelin, et al., *Nat. Struct. Biol.* 5:271-276, 1998; Fedoroff, et al., *J. Mol. Biol.* 233, 509-523, 1993; Gonzalez, et al., *Biochemistry* 34:4969-4982, 1995; Salazar, et al., *Biochemistry* 32:4207-4215, 1993). Otherwise DNA will form a default B-form helical structure. The results shown herein suggest that increased flexibility in the tracrRNA-interaction region of crRNA significantly enhances assembly of the CRISPR/Cas9 RNP. By using DNA bases, increased flexibility is achieved while maintaining an A-form-like helix. In contrast, the guide region of the crRNA should retain an A-form-like helical structure. This is preferentially achieved by maintaining a certain number of RNA bases in and overlapping the seed sequence, with the greatest activity found when all guide region nucleotides are RNA. This is likely due to the fact that the crRNA guide region binds to DNA. Too much DNA in the guide region might allow formation of competing B-form helical structure, which could displace the target phosphodiester bond from the active sites of the enzyme. Finally, the presence of this combination of flexibility in the tracrRNA-interaction region and A-form-like helical structure in the guide region may enhance the formation of CRISPR/Cas9 RNP complexes that are in the active structural state.

Figure 9A:
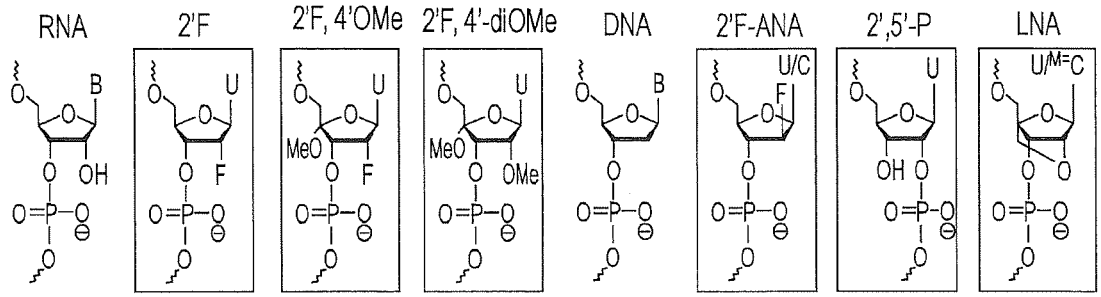
FIG. 9A and FIG. 9B show structure of certain chemically modified RNA and DNA nucleotides used in crRNAs, crRNA configurations, and cleavage activity.
Figure 9B:
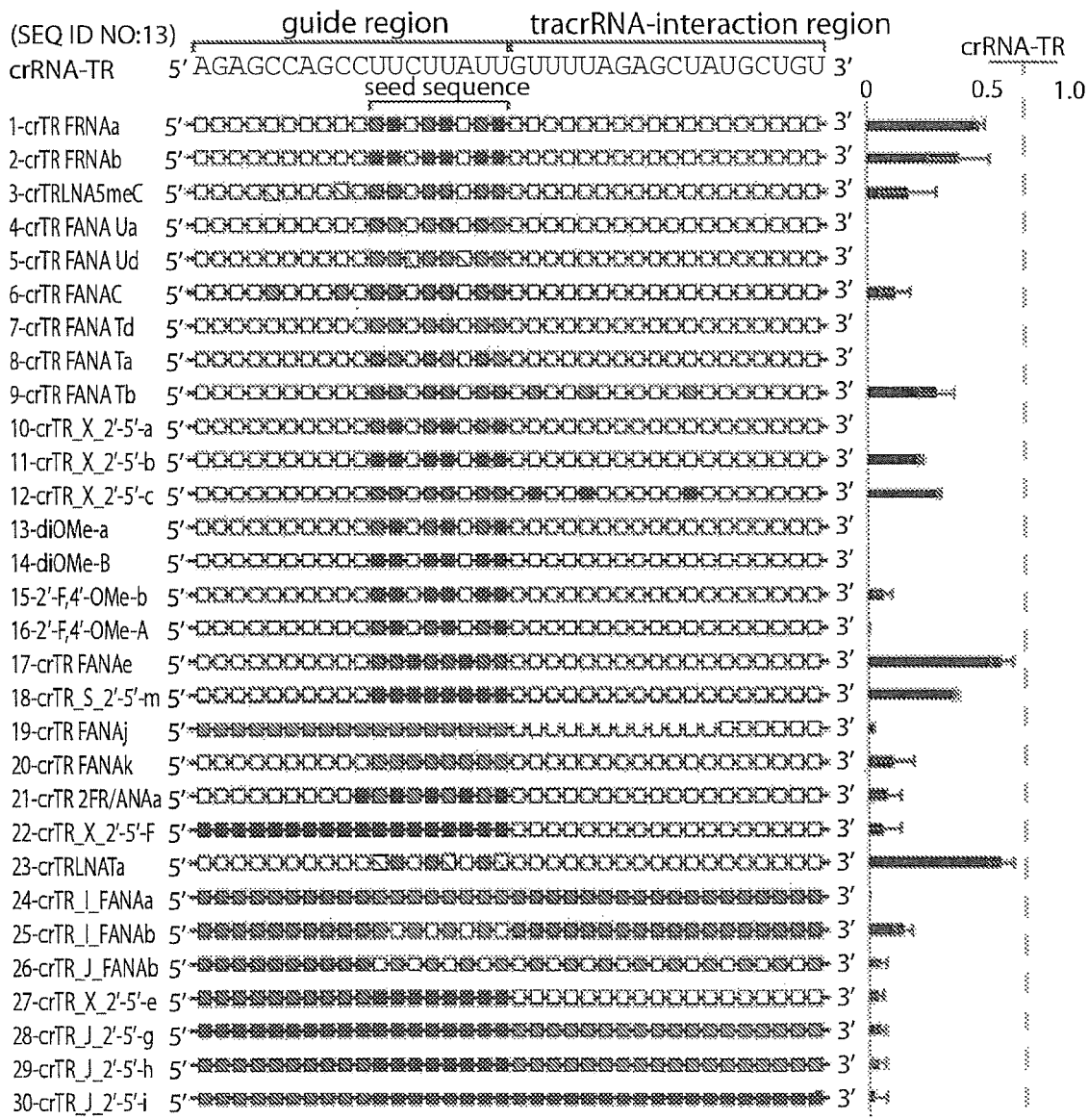
Figure 9B:
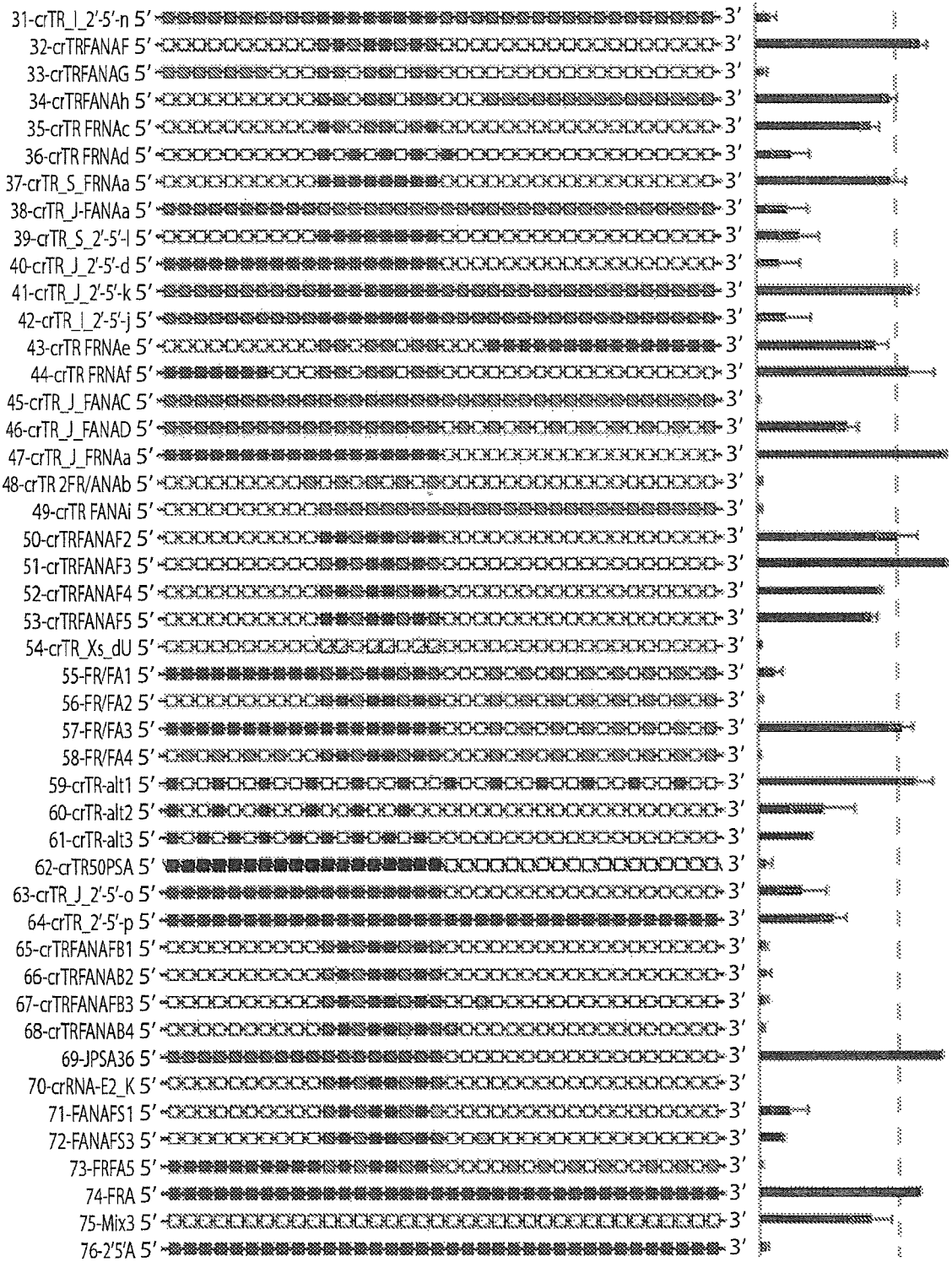

To further exemplify these findings, crRNAs with chemical modifications that might mimic the properties of RNA or DNA were synthesized (FIG. 9B). The chemical structure of a ribonucleotide (RNA), deoxyribonucleotide (DNA), and certain chemically modified nucleotides used in crRNAs is shown in FIG. 9A. Among the chemically modified nucleotides tested, 2'-fluorinated (2'F) (Cook, "Second Generation Antisense Oligonucleotides: 2'-Modifications," Vol. 33, San Diego: Academic Press, 1998), 2'-5'-linked (Wasner, et al., *Biochemistry* 37:7478-7486, 1998), locked nucleic acid (LNA) (Koshkin, et al., *J. Am. Chem. Soc.* 120:13252-13253, 1998), 2'-fluorinated,4'-O-methyl (2'F,4'OMe), 2',4'-di-fluorinated (Martinez-Montero, et al., *ACS Chem. Biol.* 10:2016-2023, 2015), and 2',4'-di-O-methyl (2',4'-diOMe) nucleotides represented nucleotides with properties similar to RNA. In contrast, 2'-fluoro-arabinonucleic acid (FANA) nucleotides were expected to mimic DNA (Damha, et al., *J. Am. Chem. Soc.* 121:12976-12977, 1998; Martin-Pintado, et al., *Nucl. Acids Res.* 40:9329-9339, 2012; Trempe, et al., *J. Am. Chem. Soc.* 123:4896-4903, 2001).

Starting with DNA substitution patterns that worked well (above), chemically-modified nucleotides were incorporated. The modified nucleotides possess various RNA or DNA "mimic" properties that can be used to alter the A-form helical structure of the native RNAs. Incorporating chemically modified nucleotides revealed important trends in CRISPR-Cas cleavage activity (FIG. 9B). Nucleotides with bulky moieties (i.e., OMe) on the C2' position of the sugar were not well-tolerated. In contrast, smaller modifications, such as fluorine atoms in place of oxygen at 2' positions, are well-tolerated. In particular, 2'-F-RNA worked very well as an RNA replacement and the 2'-stereoisomer, FANA (a DNA mimic), worked relatively well in some DNA positions. Several crRNA modification designs were found that contain no RNA but still exhibit strong cleavage activity.

Specifically it was found that replacing RNA bases with 2'F generally maintained good to excellent activity (e.g., crRNA 1, 2, 36, 37, 43, 44, 47, 57, 74; numbers correspond to those shown in FIG. 9B). DNA could sometimes be replaced in part with FANA (crRNA 6, 38, 46). Some combinations of DNA, 2'F and FANA provided excellent activity (crRNA 51, 52, 53, 54). Introducing acyclic linkers ("B") into these sequences significantly reduced activity (crRNA 65, 67, 68). In contrast, placing FANA in some RNA positions severely reduced activity (crRNA 4, 5, 7, 8, 19, 20, 21, 24, 25, 26, 55, 56, 73). The 2'-5'-linked nucleotides were largely detrimental when directly replacing RNA or DNA (crRNA 10, 11, 30, 31, 40, 42). However, when 2'-5'-linked nucleotides were used to replace RNA nucleotides at random, novel configurations (termed herein as "mixmers"), much better results were generally obtained (crRNA 18, 41, 64). Also, when 2'F nucleotides were used to replace 2',5'-linked nucleotides in the "mixmer" configuration (crRNA 75) excellent results were obtained relative to the inactive all-2',5' crRNA (crRNA 76). All complexes assembled from crRNAs with DNA/2'5'-RNA mixmer configurations were inactive (crRNA 28, 29). Approximately 40% activity was retained when three of the six RNA bases in crRNA-TR_Xs were replaced with LNA bases (crRNA 23). One novel configuration, which contained RNA, 2'F and FANA in the seed sequence and DNA everywhere else, showed very high activity (crRNA 32). Replacing RNA bases in crRNA-E2_Xs with nucleotides possessing 2'OMe and 4'OMe moieties (crRNA 13, 14, 15, 16) resulted in complete loss of activity. Complete replacement of all phosphodiester bonds with phorphorothioate bonds resulted in a very active crRNA in one instance (crRNA 69) but was detrimental to activity for another (crRNA 62). All chemically modified crRNAs were tested three or more times for cleavage of a linearized plasmid DNA target containing the TR gene.

These results have enabled the establishment of important chemical and mechanistic features of nucleotide substitution for crRNA. The results show that the crRNA requires nucleotides in the guide region that confer A-form-like helical properties and nucleotides in the tracrRNA-interaction region that provide flexibility while still allowing base-pairing with the tracrRNA that maintain A-form-like helical structure. Thus, any modified nucleotides in the crRNA guide region, including the seed sequence, that mimic the properties of RNA, preferably lacking large chemical moieties, but do not interfere with productive RNP assembly will be suitable substitutes for RNA nucleotides. These include, but are certainly not limited to, 2'F, LNA, and 2'-5' linked nucleotides. Any modified nucleotides that increase flexibility and are placed in the tracrRNA-interaction region of crRNAs enhance CRISPR/Cas9 RNP assembly and substantially increase specific cleavage activity over that of RNA nucleotides or RNA nucleotide mimics in the same tracrRNA-interaction region. These include, but are not limited to, FANA and DNA nucleotides, acyclic or unlocked nucleosides, and acyclic aliphatic linkers (Mangos and Damha, *Curr. Top. Med. Chem.* 2:1147-1171, 2002; Mangos, et al., *J. Am. Chem. Soc.* 125:654-661, 2003). Finally, novel "mixmer" configurations of 2'-5'-linked nucleotides with RNA nucleotides placed in the guide region and seed sequence afford activity. Alternating DNA-FANA or DNA-FNA mixmers also confer excellent cleavage activity when placed in the tracrRNA-interaction region of crRNA.

Example 17

Cell-based Editing

To measure genome editing with chemically modified crRNAs, RNP complexes were assembled in vitro and transfected into human tissue culture cells. CRISPR-Cas9 enzyme complexes were assembled with purified Cas9 enzymes and synthetic RNA and chemically-modified guides. Assembled RNP complexes were then mixed with lipid (CRISPR-MAX) transfection reagent and single-stranded donor DNA, and added to commercially available HeLa T-REx cells. These cells contain a single genomically integrated tetracycline receptor (TR) gene. Donor DNA consists of a 21 nucleotide barcode sequence flanked by 40 nucleotides that match the sequences flanking the genomic target cut site. During HDR, the barcode from the co-transfected donor DNA sequence will be inserted into the genome at the cut site.

Editing was measured 48 hr after transfection. First genomic DNA was isolated from cells and quantified by quantitative PCR (qPCR). Next, using the same amount of genomic DNA for all reactions, PCR was performed using a set of PCR primers that flank the genomic insertion site. Upon electrophoresis a higher molecular weight band was observed that can be quantified. The ratio of upper to lower bands estimates % HDR editing. Using this approach robust HDR with DNA-substituted crRNAs was demonstrated (FIG. 10A), as well as for certain chemically modified crRNAs lacking RNA bases (FIG. 10B). To ensure that the PCR products observed were indeed the expected products with the correct barcode sequence, the PCR product was extracted and sequenced. Results revealed insertion exactly as expected (FIG. 10C). These studies demonstrate that chemically modified crRNAs are capable of directing genome editing inside of human cells.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a Cas9 protein, a first oligonucleotide comprising a first region having a 5' end and a 3' end and a second region, and a second oligonucleotide comprising a first region and a second region, wherein said second region of said first oligonucleotide interacts with said first region of said second oligonucleotide, and said second region of said second oligonucleotide interacts with said Cas9 protein, wherein all nucleotides of said first oligonucleotide are 2'-deoxyribonucleotides or 2'-deoxyribonucleotide analogs.

2. The composition of claim 1, wherein said first oligonucleotide comprises the chemical structure of crRNA_K.

3. The composition of claim 1, wherein said first oligonucleotide comprises at least a first 2'-fluoroarabinonucleotide.

4. The composition of claim 1, wherein said Cas9 protein comprises at least a first mutation that inactivates said Cas9 protein.

5. The composition of claim 4, wherein said Cas9 protein comprises a D10A or a H840A mutation.

6. The composition of claim 5, wherein said Cas9 protein comprises a D10A and a H840A mutation.

7. A method of binding a double-stranded DNA without cleaving said double-stranded DNA, comprising contacting said double-stranded DNA with the composition of claim 1.

8. The method of claim 7, wherein said first oligonucleotide comprises at least a first 2'-fluoroarabinonucleotide.

9. A method of inhibiting transcription of a double-stranded DNA, comprising contacting said double-stranded DNA with the composition of claim 1.

10. The method of claim 9, wherein said first oligonucleotide comprises at least a first 2'-fluoroarabinonucleotide.

11. The method of claim 9, wherein said double-stranded DNA is located in a cell.

12. A method of activating transcription of a double-stranded DNA, comprising contacting said double-stranded DNA with the composition of claim 1.

13. The method of claim 12, wherein said first oligonucleotide comprises at least a first 2'-fluoroarabinonucleotide.

14. The method of claim 12, wherein said double-stranded DNA is located in a cell.

* * * * *

SEQUENCE LISTING

<160> NUMBER OF SEQ ID NOS: 16

<210> SEQ ID NO 1
<211> LENGTH: 38
<212> TYPE: RNA
<213> ORGANISM: ARTIFICIAL SEQUENCE
<220> FEATURE:
<223> OTHER INFORMATION: oligonucleotide

```
<220> FEATURE:
<221> NAME/KEY: misc_feature
<222> LOCATION: (1)..(20)
<223> OTHER INFORMATION: n is a, c, g, or u

<400> SEQUENCE: 1
nnnnnnnnnn nnnnnnnnnn guuuuagagc uaugcugu                            38

<210> SEQ ID NO 2
<211> LENGTH: 67
<212> TYPE: RNA
<213> ORGANISM: ARTIFICIAL SEQUENCE
<220> FEATURE:
<223> OTHER INFORMATION: OLIGONUCLEOTIDE

<400> SEQUENCE: 2
acagcauagc aaguuaaaau aaggcuaguc cguuaucaac uugaaaaagu ggcaccgagu    60
cggugcu                                                              67

<210> SEQ ID NO 3
<211> LENGTH: 97
<212> TYPE: RNA
<213> ORGANISM: ARTIFICIAL SEQUENCE
<220> FEATURE:
<223> OTHER INFORMATION: OLIGONUCLEOTIDE
<220> FEATURE:
<221> NAME/KEY: misc_feature
<222> LOCATION: (1)..(20)
<223> OTHER INFORMATION: n is a, c, g, or u

<400> SEQUENCE: 3
nnnnnnnnnn nnnnnnnnnn guuuuagagc uagaaauagc aaguuaaaau aaggcuaguc    60
cguuaucaac uugaaaaagu ggcaccgagu cggugcu                             97

<210> SEQ ID NO 4
<211> LENGTH: 42
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 4
taccagcaaa acacuccgau guuuuagagc uaugcuguuu ug                       42

<210> SEQ ID NO 5
<211> LENGTH: 42
<212> TYPE: RNA
<213> ORGANISM: ARTIFICIAL SEQUENCE
<220> FEATURE:
<223> OTHER INFORMATION: OLIGONUCLEOTIDE

<400> SEQUENCE: 5
uaccagcaaa acacuccgau guuuuagagc uaugcuguuu ug                       42

<210> SEQ ID NO 6
<211> LENGTH: 69
<212> TYPE: RNA
<213> ORGANISM: ARTIFICIAL SEQUENCE
<220> FEATURE:
<223> OTHER INFORMATION: OLIGONUCLEOTIDE

<400> SEQUENCE: 6
aaacagcaua gcaaguuaaa auaaggcuag uccguuauca acuugaaaaa guggcaccga    60
gucggugcu                                                            69
```

<210> SEQ ID NO 7
<211> LENGTH: 69
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 7
aaacagcata gcaagttaaa ataaggctag tccgttatca acttgaaaaa gtggcaccga    60
gtcggugct                                                            69

<210> SEQ ID NO 8
<211> LENGTH: 67
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 8
acagcatagc aagttaaaat aaggcuaguc cguuaucaac uugaaaaagu ggcaccgagu    60
cggugcu                                                              67

<210> SEQ ID NO 9
<211> LENGTH: 66
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 9
acagcatagc aaguuaaaau aaggcuagtc cguuatcaac ttgaaaaagt ggcaccgagu    60
cggtgc                                                               66

<210> SEQ ID NO 10
<211> LENGTH: 66
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 10
acagcauagc aaguuaaaau aaggctagtc cguuatcaac ttgaaaaagt ggcaccgagu    60
cggtgc                                                               66

<210> SEQ ID NO 11
<211> LENGTH: 66
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 11
acagcauagc aaguuaaaau aaggctagtc cgttatcaac ttgaaaaagt ggcaccgagt    60
cggtgc                                                               66

<210> SEQ ID NO 12
<211> LENGTH: 42
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 12

```
uaccagcaaa acacuccgau gttttagagc tatgctgttt tg                42
```

<210> SEQ ID NO 13
<211> LENGTH: 36
<212> TYPE: RNA
<213> ORGANISM: ARTIFICIAL SEQUENCE
<220> FEATURE:
<223> OTHER INFORMATION: OLIGONUCLEOTIDE

<400> SEQUENCE: 13

```
agagccagcc uucuuauugu uuuagagcua ugcugu                      36
```

<210> SEQ ID NO 14
<211> LENGTH: 68
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 14

```
accaaggtgc agagccagcc ttcttattcg gccttgaatt gatcatatgc ggattagaaa    60
aacaactt                                                             68
```

<210> SEQ ID NO 15
<211> LENGTH: 89
<212> TYPE: DNA
<213> ORGANISM: ARTIFICIAL SEQUENCE
<220> FEATURE:
<223> OTHER INFORMATION: OLIGONUCLEOTIDE

<400> SEQUENCE: 15

```
accaaggtgc agagccagcc ttctttgctg ccctggatgt tgttaaattc ggccttgaat    60
tgatcatatg cggattagaa aaacaactt                                      89
```

<210> SEQ ID NO 16
<211> LENGTH: 89
<212> TYPE: DNA
<213> ORGANISM: ARTIFICIAL SEQUENCE
<220> FEATURE:
<223> OTHER INFORMATION: OLIGONUCLEOTIDE
<220> FEATURE:
<221> NAME/KEY: misc_feature
<222> LOCATION: (1)..(17)
<223> OTHER INFORMATION: n is a, c, g, or t

<400> SEQUENCE: 16

```
nnnnnnnnnn nnnnnnngcc ttctttgctg ccctggatgt tgttaaattc ggccttgaat    60
tgatcatatg cggattagaa aaacaactt                                      89
```